US012233046B2

(12) United States Patent
Mandell et al.

(10) Patent No.: US 12,233,046 B2
(45) Date of Patent: Feb. 25, 2025

(54) PSYCHOACTIVE MEDICINES AND THEIR USE FOR TREATING PSYCHIATRIC AND NEUROLOGICAL CONDITIONS AND DISORDERS

(71) Applicant: Transcend Therapeutics, Inc., New York, NY (US)

(72) Inventors: Blake Mandell, Brooklyn, NY (US); Martin Stogniew, Lakewood Ranch, FL (US); Jennifer Louise Schmidt, Garden City, NY (US)

(73) Assignee: TRANSCEND THERAPEUTICS, INC., New York, NY (US)

( * ) Notice: Subject to any disclaimer, the term of this patent is extended or adjusted under 35 U.S.C. 154(b) by 0 days.

(21) Appl. No.: 18/659,413

(22) Filed: May 9, 2024

(65) Prior Publication Data

US 2024/0293357 A1    Sep. 5, 2024

Related U.S. Application Data

(63) Continuation of application No. 18/215,547, filed on Jun. 28, 2023, now Pat. No. 12,059,402, which is a continuation of application No. 17/887,962, filed on Aug. 15, 2022, now Pat. No. 11,707,446, which is a continuation of application No. PCT/US2022/074369, filed on Aug. 1, 2022.

(60) Provisional application No. 63/230,237, filed on Aug. 6, 2021, provisional application No. 63/240,113, filed on Sep. 2, 2021, provisional application No. 63/255,706, filed on Oct. 14, 2021, provisional application No. 63/325,757, filed on Mar. 31, 2022, provisional application No. 63/328,343, filed on Apr. 7, 2022.

(51) Int. Cl.
  *A61K 31/36*   (2006.01)
  *A61K 45/06*   (2006.01)
  *A61P 25/22*   (2006.01)
  *A61P 25/24*   (2006.01)

(52) U.S. Cl.
  CPC ............ *A61K 31/36* (2013.01); *A61K 45/06* (2013.01); *A61P 25/22* (2018.01); *A61P 25/24* (2018.01)

(58) Field of Classification Search
  CPC ........... A61K 31/36; A61P 25/22; A61P 25/24
  See application file for complete search history.

(56) References Cited

U.S. PATENT DOCUMENTS

| | | |
|---|---|---|
| 2012/0108510 A1 | 5/2012 | Young et al. |
| 2014/0045884 A1 | 2/2014 | Schultz |
| 2015/0306136 A1 | 10/2015 | Meloni et al. |
| 2019/0046499 A1 | 2/2019 | Segreti |
| 2023/0054211 A1 | 2/2023 | Mandell et al. |
| 2023/0218570 A1* | 7/2023 | Dariani ............... A61K 31/198 514/464 |

FOREIGN PATENT DOCUMENTS

| | | | |
|---|---|---|---|
| WO | WO-9639133 A1 * | 12/1996 | ........... C07D 317/66 |
| WO | WO 2021/257500 | 12/2021 | |
| WO | WO 2023/081403 | 5/2023 | |

OTHER PUBLICATIONS

Ciechomksa et al., "Activity and Biotransformation of Three Synthetic "Legal Highs": Mephedrone, Methylone and 3,4-Methylenodioxypyrovalerone", Problems of Forensic Sciences (2012) 89:71-85.
Shao et al., "Psilocybin induces rapid and persistent growth of the dendritic spines in frontal cortex in vivo", Neuron, Aug. 18, 2021; 109:2535-2544.
Porsolt et al., "Depression: a new animal model sensitive to antidepressant treatments", Nature (1977) 266:730-732.
Borsini et al., "Is the forced swimming test a suitable model for revealing antidepressant activity?", Psychopharmacology (1988) 94:147-160.
Detke et al., "Active behaviors in the rat forced swimming test differentially produced by serotonergic and noradrenergic antidepressants", Psychopharmacology (1995) 121:66-72.
Hibicke et al., "Psychedelics, but Not Ketamine, Produce Persistent Antidepressant-like Effects in a Rodent Experimental System for the Study of Depression", ACS Chem. Neurosci., Mar. 2020, 11:864-871.
Yang et al., "Acute administration of ketamine in rats increases hippocampal BDNF and mTOR levels during forced swimming test", Upsala Journal of Medical Sciences, 2013, 118(1): 3-8.
Tizabi et al., "Antidepressant-Like Effects of Low Ketamine Dose is Associated with Increased Hippocampal AMPA/NMDA Receptor Density Ratio in Female Wistar-Kyoto Rats", Neuroscience (2012) 213:72-80.
Weston et al., "Repeated Dosing of Ketamine in the Forced Swim Test: Are Multiple Shots Better Than One?", Frontiers in Psychiatry, May 2021, 12:659052.
Majumder et al., "Antidepressant-like effects of 3,4-methylenedioxymethamphetamine in an animal model of depression", Behavioural Pharmacology (2011) 22:758-765.

(Continued)

*Primary Examiner* — Kevin E Weddington
(74) *Attorney, Agent, or Firm* — PEARL COHEN ZEDEK LATZER BARATZ LLP

(57) ABSTRACT

The invention relates to psychoactive medicines including 2C-B, methylone, MBDB, their respective metabolites, isomers, enantiomers, polymorphs, and analogues (2C-series and cathinones); their preparation, formulations, intermediates, routes of administration, dosing and schedule for medical uses for psychiatric and neurological conditions and disorders.

29 Claims, 12 Drawing Sheets

(56) References Cited

OTHER PUBLICATIONS

Feduccia et al., "Discontinuation of medications classified as reuptake inhibitors affects treatment response of MDMA-assisted psychotherapy", Psychopharmacology, Nov. 2020, 238:581-588.
Wicking et al., "Deficient fear extinction memory in posttraumatic stress disorder", Neurobiology of Learning and Memory (2016) 136:116.
Pedraza et al., "Chronic fluoxetine prevents fear memory generalization and enhances subsequent extinction by remodeling hippocampal dendritic spines and slowing down system consolidation", Translational Psychiatry (2019) 9:53.
Feduccia et al., "MDMA-assisted psychotherapy for PTSD: Are memory reconsolidation and fear extinction underlying mechanisms?", Progress in Neuropsychopharmacology & Biological Psychiatry (2018) 84:221-228.
Young et al., "3,4-Methylenedioxymethamphetamine facilitates fear extinction learning", Translational Psychiatry (2015) 5:e634.
Den Hollander et al., "Long-term cognitive and neurochemical effects of "bath salt" designer drugs methylone and mephedrone", Pharmacology, Biochemistry and Behavior (2013) 103:501-509.
Lopez-Arnau et al., "Repeated doses of methylone, a new drug of abuse, induce changes in serotonin and dopamine systems in the mouse", Psychopharmacology (2014) 231:3119-3129.
Karila et al., "The effects and risks associated to mephedrone and methylone in humans: A review of the preliminary evidences", Brain Research Bulletin (2016) 126:61-67.
International Search Report and Written Opinion, dated Dec. 13, 2022, from corresponding International Application No. PCT/US22/74369.
Reisman, "PTSD Treatment for Veterans: What's Working, What's New, and What's Next", P&T, Oct. 2016, 41(10):623-634.
Sande, M., "Characteristics of the use of 3-MMC and other new psychoactive drugs in Slovenia, and the perceived problems experienced by users", International Journal of Drug Policy, (2016) 27:65-73.
International Search Report and Written Opinion, dated Jul. 10, 2023, from corresponding International Application No. PCT/US23/12196.
Hollander et al., "Long-term cognitive and neurochemical effects of "bath salt" designer drugs methylone and mephedrone", Pharmacology, Biochemistry and Behavior, 103: 501-509 (2013).
Molendijk et al., "Coping with the forced swim stressor: Current state-of-the-art", Behavioral Brain Research, 364: 1-10 (2019).
Anyan et al., "Too Depressed to Swim or Too Afraid to Stop? A Reinterpretation of the Forced Swim Test as a Measure of Anxiety-Like Behavior", Neuropsychopharmacology, 43: 931-933 (2018).
Stefkova et al., "Pharmacokinetic, Ambulatory, and Hyperthermic Effects of 3,4-Methylenedioxy-N-Methylcathinone (Methylone) in Rats", Frontiers in Psychiatry, vol. 8, Article 232, (2017).
Berquist et al., "In vivo effects of 3,4-methylenedioxymethamphetamine (MDMA) and its deuterated form in rodents: Drug discrimination and thermoregulation", Drug and Alcohol Dependence, Jan. 2020; 208:107850.

* cited by examiner

*Figure 2*
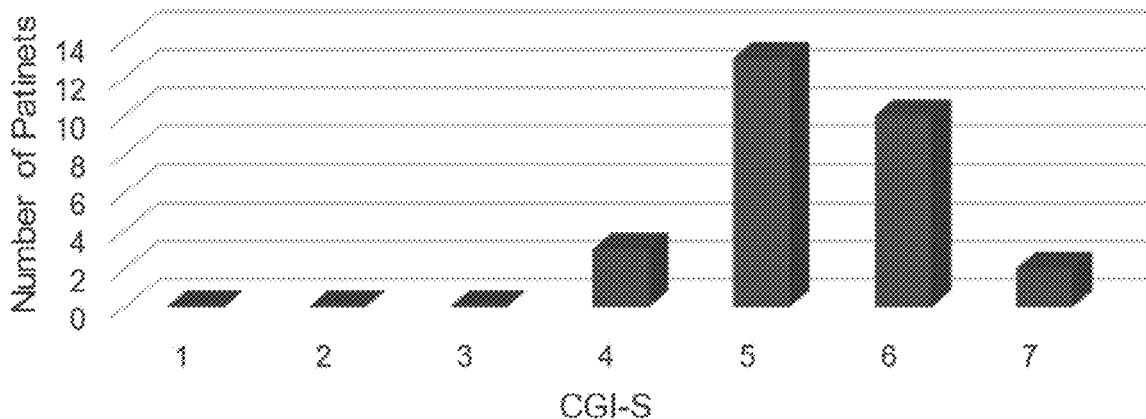
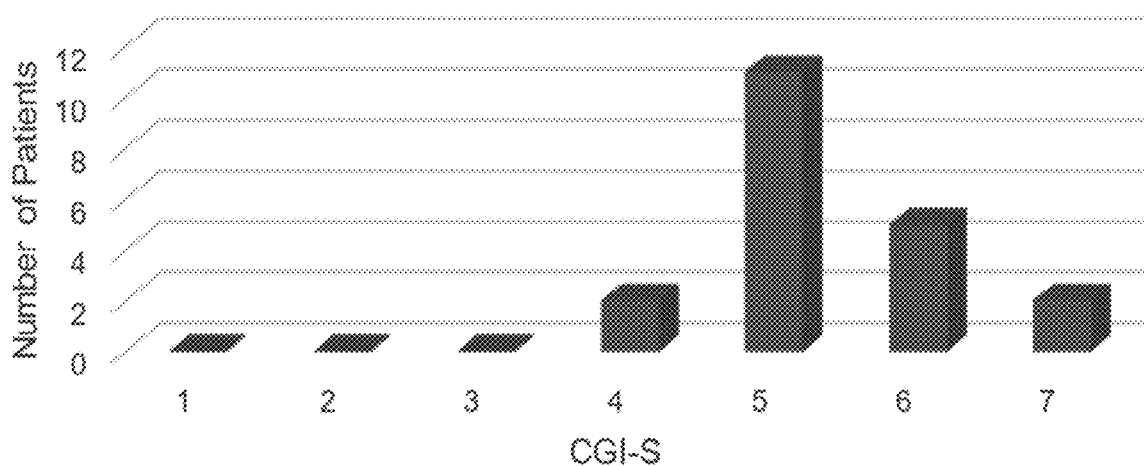
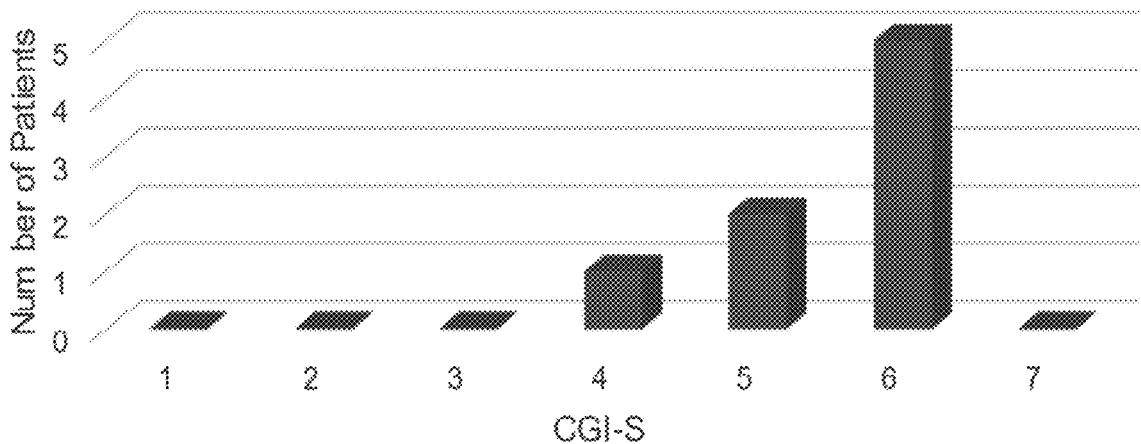

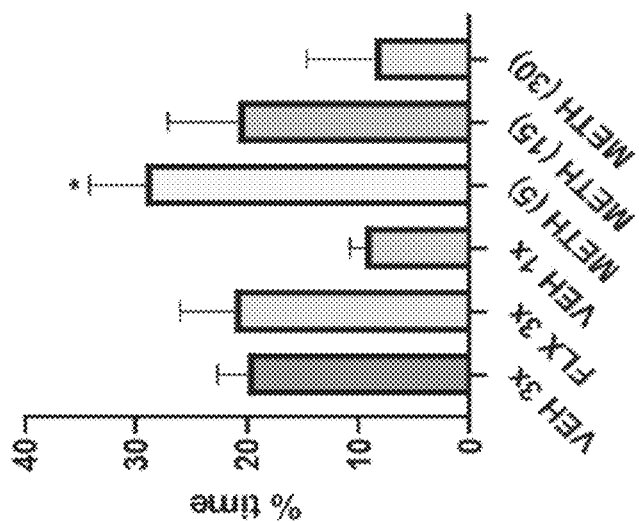
*Figure 5C* Climbing
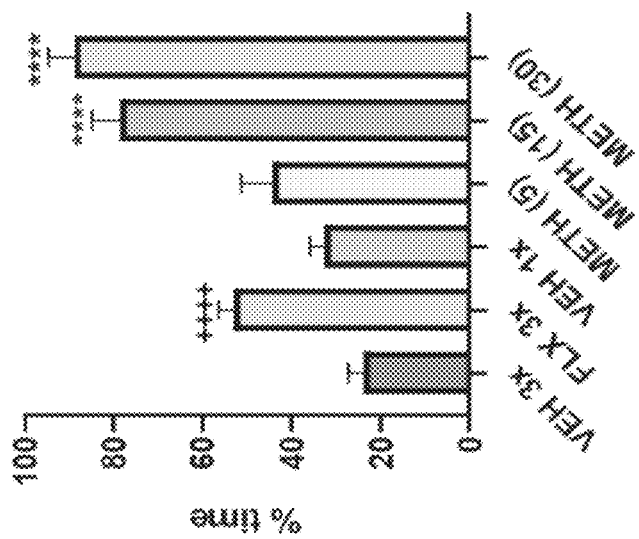
*Figure 5B* Swimming
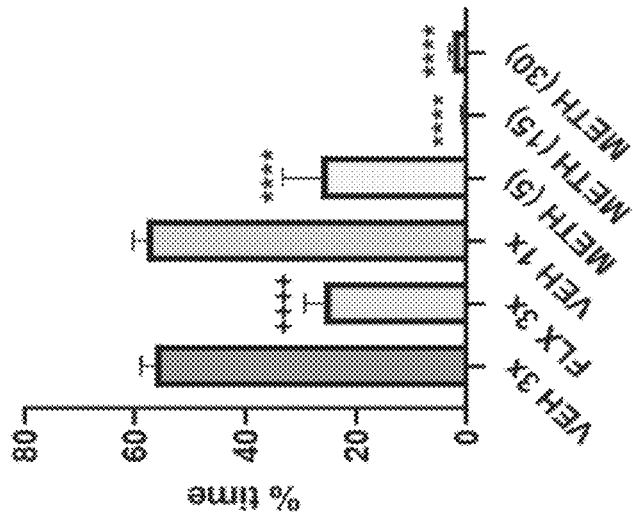
*Figure 5A* Immobility

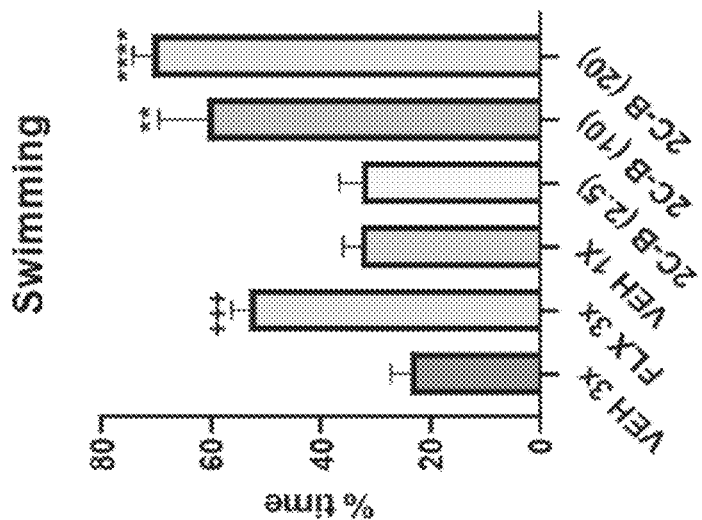
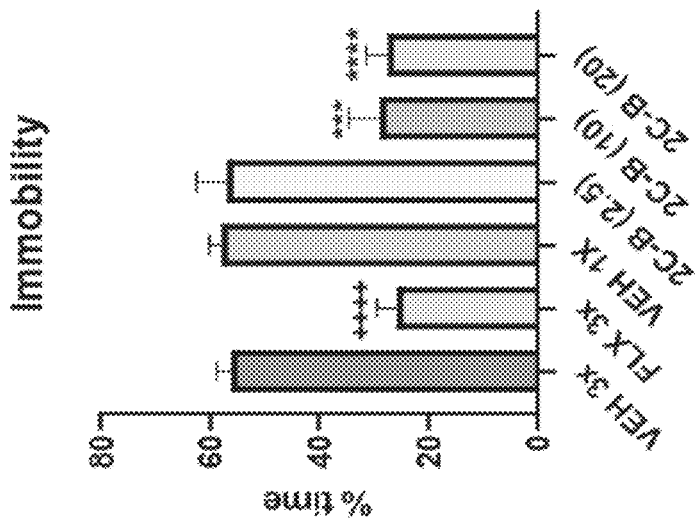

PSYCHOACTIVE MEDICINES AND THEIR USE FOR TREATING PSYCHIATRIC AND NEUROLOGICAL CONDITIONS AND DISORDERS

CROSS-REFERENCE TO RELATED APPLICATIONS

This application is a continuation of U.S. patent application Ser. No. 18/215,547, filed Jun. 28, 2023, which is a continuation of U.S. patent application Ser. No. 17/887,962, filed Aug. 15, 2022 (now U.S. Pat. No. 11,707,446), which is a continuation of International Application No. PCT/US22/74369, filed Aug. 1, 2022, which claims the benefit of U.S. Patent Application Nos. 63/230,237, filed Aug. 6, 2021, 63/240,113, filed Sep. 2, 2021, 63/255,706, filed Oct. 14, 2021, 63/325,757, filed Mar. 31, 2022, and 63/328,343, filed Apr. 7, 2022, which are hereby incorporated by reference.

FIELD OF THE INVENTION

The invention relates to psychoactive medicines including methylone, 2C-B, MBDB, their respective metabolites, isomers, enantiomers, polymorphs, and analogues (2C-series and cathinones); their preparation, formulations, intermediates, routes of administration, dosing and schedule for medical uses, and for psychiatric and neurological conditions and disorders.

BACKGROUND OF THE INVENTION

Classical psychedelics are a class of mixed serotonergic-, noradrenergic-, and dopaminergic-modulating compounds, generally of ethnobotanical provenance. These heterogenous agents are psychoactive and can alter perception, mood, and numerous other cognitive and physiological processes. Anthropological study suggests their ritual use in societies ranging from the Ancient Near East, the Mediterranean Basin, and Mesoamerica. After the discovery and synthesis of the tryptamine analogue lysergic acid-N,N-diethylamide (LSD) by Albert Hofmann in 1943, there followed decades of promising clinical development and therapeutic exploration. However, the entire class of compounds was restricted from mainstream scientific circles, e.g., in the United States by the "Controlled Substances Act" in 1970 and characterized as having "no medical use."

The incidence of neuropsychiatric disorders such as treatment-resistant depression, fibromyalgia, and post-traumatic stress disorder (PTSD) is growing, and there have been a dearth of new treatments that meaningfully impact patients' lives. The dissociative anesthetic ketamine, namely its enantiomer esketamine, was first approved in 2019 as Spravato for major depressive disorder (MDD) and/or suicidality. As of May 2021, there are three FDA Breakthrough Therapy designations for psychedelic medicines: 3,4-Methylenedioxymethamphetamine (MDMA) for PTSD and psilocybin for both treatment-resistant depression (TRD) and MDD. There is increasing recognition of the limited effectiveness of current pharmacological interventions, coupled with the need for new psychoactive medicines without provider-intensive safety and monitoring issues, or contraindicated in patients on existing medications such as selective-serotonin reuptake inhibitors (SSRIs) and other drug classes.

A Phase 3 trial investigating MDMA (3,4-methylenedioxy-N-methylamphetamine) in patients with severe PTSD revealed an acceptable efficacy and safety profile. There has been recent evidence for the efficacy of psilocybin in major depressive disorder (MDD). Psilocybin is a psychoactive alkaloid produced by more than 200 mushroom species, with some evidence of fast-acting antidepressant properties. In recent clinical trials with psilocybin, MDD patients varied in treatment needs from a single dose to monthly doses but with similar efficacy and safety. While psilocybin and MDMA offer hope to patients without other treatment options, it is estimated that they may only benefit 5-10% of patients in need.

The identification of manipulations that reopen critical periods has been a priority for translational neuroscience. Many neuropsychiatric disease states are believed to be developmentally related to the closure of "critical periods," early intervals of the lifespan when the nervous system is more sensitive, to healthy (or harmful) environmental stimuli required for proper circuit organization and learning. The closure of critical periods limits the brains' ability to adapt even when optimal conditions are restored. Agonists of the family of 5-hydroxytryptamine (5-HT) serotonin receptors, including MDMA, DMT, and mescaline, increase levels of oxytocin—which is involved in social function and which animal models suggest may open a critical window in cortical functioning—allowing learning of new behavioral responses. These oxytocin receptors in the nucleus accumbens (NAc) are activated via $5\text{-HT}_{1B}$ receptors in medium spiny neurons of the dorsal raphe nuclei, blockade of which prevents social reward learning.

Mescaline (3,4,5-trimethoxyphenethylamine), an ancient-precursor of modern synthetic phenethylamine 2-CB (2,5-dimethoxy-4-bromophenethylamine), is derived from the crown-buttons of the peyote cactus native to Mexico and southwestern Texas. Mescaline closely resembles the catecholamine-signaling molecules dopamine and noradrenaline after one methylation step; its psychoactive properties may stem from this structural similarity. Most novel psychoactive compounds still fit within familiar neuro-chemotype classes and have overlapping pharmacology with their classic predecessors. A long-standing hypothesis is that these agents, especially phenylalkylamines, are most selective for two receptors: $5\text{-HT}_{2A}$ and $5\text{-HT}_{2C}$, out of more than 50 neurotransmitter receptor subclasses.

MBDB (N-methyl-1-(1,3-benzodioxol-5-yl)-2-aminobutane) is the alpha-ethyl homologue of MDMA, which was synthesized by multiple medicinal chemistry groups in the 1980s. MBDB is a prototypical member of the "entactogen" class, currently not Schedule I in the United States, which combines two structural features that attenuate binding at monoamine receptors: N-methylation and alpha-ethylation. MBDB quickly became a recreational drug incorporated as a component of "Ecstasy" pills, along with MDMA and other synthetic cathinones. In two retrospective reports of polydrug overdose deaths associated with MBDB (where alcohol and cannabis levels were also measured), blood concentration of 0.435 and 1.2 mg/L were measured. In a meta-analysis of MDMA overdose deaths, 13 of 77 deaths directly attributable to the toxic effects of MDMA alone measured blood concentrations in a range of 0.478-53.9 mg/L-which are comparable to the presumed toxic MBDB levels. Furthermore, in an animal model (±)-MBDB·HCl (25 mg/kg) was injected IP every 12 hours for 4 days, with (±)-MDMA·HCl (20 mg/kg) for comparison. Based on loss of 5-HT/5-HIAA uptake sites, the multiple dose regimen employed in this study apparently destroyed 55 to 60% of the serotonergic terminals in the cortex and hippocampus, without significantly altering the catecholamines or their metabolites at 2 weeks post-treatment. These results show that after multiple dosing with MBDB, a decrease in indices associated with serotonergic function has occurred. This neurotoxic effect was somewhat less than that seen with behaviorally equipotent doses of MDMA.

Synthetic cathinones, such as methylone (3,4-methylenedioxy-N-methylcathinone), are psychomotor stimulants that exert their effects by altering the function of plasma membrane transporters for serotonin, dopamine, and norepinephrine. Individual cathinones may vary in their potencies on each of the three monoamine neurotransmitter pathways. Naturally occurring cathinone, an alkaloid structurally similar to amphetamine, was originally extracted from the fresh leaves of the *Catha edulis* or khat plant, chewed in east Africa and the Arabian Peninsula. Synthetic structural modifications of cathinone have led to a number of "designer" derivatives that are commonly sold as "bath salts" through illicit distribution. These cathinone derivatives—classified chemically as β-ketoamphetamines—include methylone, ethylone, butylone, mephedrone, and 3,4-methylenedioxypyrovalerone (MDPV), and act synergistically at the human dopamine transporter. Cathinones and the other related classes of phenethylamines both behave as Central Nervous System (CNS) stimulants; however, cathinones usually have a lower potency than the corresponding phenethylamine analogue, since the β-keto group creates a more polar molecule that is less able to cross the blood-brain barrier.

Methylone's affinity for the vesicular monoamine transporter 2 (VMAT2) is about 13× lower than that of MDMA. However, there is some mixed evidence: assays for plasmalemmal and vesicular monoamine transporters in a mouse model of locomotor activity found methylone to be a more potent 5-HT and dopamine uptake inhibitor than MDMA. After intraperitoneal administration in rats, methylone peaks in brain and serum concentration in 15-30 minutes, with a half-life of about 1-2 hours. By contrast, MDMA's half-life ranges from 5-7 hours depending on the animal model used and dosing conditions.

In humans, SSRIs also diminish or prevent the therapeutic effects of MDMA due to substrate competition: side-effects such as increased blood pressure (BP) and hyperthermia are partially due to an interaction of MDMA with the serotonin carrier. This is another important consideration when thinking about use as a rapid-onset antidepressant or augmentation therapy. Previous research studies have found an association between MDMA use and symptoms of depression or anxiety. The difficulty of assessing the causation or connection between MDMA and depression is increased given that pre-existing psychiatric problems occur in people who choose to use MDMA. A meta-analysis detected an association between MDMA use and self-reported depression symptom. The range of pharmacogenetic variation in MDMA metabolism also increases risk for depression in a sizable number of patients.

Animal studies to address the psychological impacts of MDMA tested a 10 mg/kg dose for 10 days in rats; measures of anxiety-like behaviors, such as open-field ambulation, indicated an increase in anxious phenotypes 3 months later. A dose of 5 mg/kg of MDMA given to rats 4 times in 4 hours, on 2 consecutive days, diminished responses (active and passive) on the forced swim test and increased immobility up to 12 weeks post-MDMA exposure—indicating possibly long-term negative behavioral changes. Fluoxetine treatment reversed MDMA-induced anxiety in the emergence test and immobility duration in the forced swim test, yet exhibited no effects on the social interaction test. This study also analyzed post-mortem levels of 5-HT and its metabolite, 5-hydroxyindoleacetic acid (5-HIAA), with both being decreased in cortical areas of MDMA-treated rats. Fluoxetine treatment did not greatly affect 5-HT levels in MDMA pretreated rats, but significantly decreased 5-HIAA levels in all brain sites examined. This can be interpreted as MDMA-induced chronic depletion of 5-HT, leading to anxious or depressed phenotypes.

Other mechanisms include acute MDMA-induced 5-HT release from serotonergic terminals, in conjunction with inhibition of 5-HT reuptake, which result in marked depletions of both 5-HT and 5-HIAA. This has been reported in postmortem brain tissue of humans, as well as in vivo from cerebrospinal fluid (CSF) measurements. Following the monoamine theory of depression this data is discouraging, although studies are somewhat confounded: the evidence highlights a discrepancy between the acute and chronic pharmacology of MDMA. While acutely, MDMA works to increase 5-HT availability, suggestive of rapid-onset antidepressant properties and positive changes to emotion, this transient effect may be accompanied by later depletions of 5-HT. There is anecdotal human experience to support depleted 5-HT stores at doses that would be used therapeutically.

Reduced levels of 5-HT and its metabolites in brain tissue and the CSF have also been interpreted to indicate that MDMA is neurotoxic, assessed in vivo. Incidentally, a low SERT density is also associated with depression. Considering reduced SERT density in animal literature, the parsimonious interpretation is that repeated exposure to MDMA in humans, even in moderate amounts, leads to damage in 5-HT neuron terminals innervating the cortex. Furthermore, alterations in mood, cognition, and impulse control associated with these changes might contribute to sustain MDMA use.

These and other discrepancies in MDMA's neurotoxicity data remain unresolved, making it unlikely that MDMA will be explored as a mainstream antidepressant; especially when 5-HT neurotransmitter circuits are implicated in both depression pathophysiology and MDMA neurotoxicity. In recent PTSD Phase 2 MDMA trials, there were cases of depression/MDD logged as adverse events at doses of 125 mg and 150 mg, some of which continued during long-term follow up. Anxiety and severe suicidal ideation were also logged. And before it progressed to Phase 3, the hypothesis that MDMA had potential efficacy as a rapid-onset antidepressant had been explored. However, MDMA, psilocybin and the other classic psychedelics mentioned have at least the following limitations in reaching the hundreds of millions of people suffering from treatment-resistant neuropsychiatric illness:

1) Safety: Given their strong serotonin agonism, they are contraindicated in patients on SSRIs and many other psychiatric medications, due to a risk of serotonin syndrome. This would prevent many, if not most, patients suffering from neuropsychiatric illness from accessing these agents. Furthermore, MDMA causes multiple forms of arrhythmia and dilated cardiomyopathy with prolonged use, potentially resulting in ventricular fibrillation and asystole, and is contraindicated in preexisting dysrhythmias or pulmonary disease.
2) Combination: Patients whose disorders are treatment-resistant have often tried SSRIs/serotonin-norepinephrine reuptake inhibitors (SNRIs)/tricyclic antidepressants (TCAs)/etc. Weaning patients off SSRIs and other antidepressant medications takes a minimum of 6 weeks. Therefore, developing psychoactive analogues which minimize adverse interactions—and are additive in therapeutic effects—would be a compelling benefit for patients in need. It would be unfortunate if those who benefit most from psychoactive medications are hindered by their past or current treatment-regimens.

3) Care delivery/Ease of Use: Psychoactive treatment is ideally administered by oneself at home or with minimal supervision. Access to MDMA and psilocybin is limited by the amount of time each administration requires, the hours of provider and safety-sitter time, and the training and licensure requirements. In addition to preparation and integration psychotherapy sessions, MDMA and psilocybin have long dosing sessions (up to 8 hours). Likewise, ketamine by IV infusion requires 3-4 hour clinic visits with physician-administration and supervision, accompanied with intensive psychotherapy.

4) Patient desirability: Many patients are unwilling to undergo treatments with classical psychedelics and entactogens like psilocybin and MDMA. For these treatments, clinical outcomes may rely on profound subjective experiences that are often challenging, discomforting, or scary.

Thus, there is a need for CNS medications, including antidepressants and PTSD treatments, with mainstream potential, better safety and efficacy, faster acting effect profile, fewer drug-drug interactions, and/or more effective in combination therapy. The prevalence of Any Mental Illness (AMI) among US adults is greater than 50 million, representing >20% of the population. The gap between the disease burden and effective treatments is widening. Despite its adverse effects, Wellbutrin (bupropion), an atypical triple-reuptake inhibitor (norepinephrine-dopamine reuptake inhibitor, nicotinic receptor antagonist), remains one of the most widely prescribed antidepressants (24 million prescriptions in 2018). Bupropion is often used in adjunct to SSRIs, and it has also been shown to have positive results in treating anxiety associated with depression compared with sertraline and fluoxetine. Bupropion is reported to be used off label in addition to other medications to treat panic disorder. However, bupropion side effects include >23% increase in chance of congenital heart defects in children in the first trimester of pregnancy, along with a constellation of neurogenic side effects such as anxiety, abdominal pain, agitation, insomnia, headache/migraine, nausea/vomiting, constipation, tremor, dizziness, excessive sweating, blurred vision, tachycardia, confusion, rash, hostility, cardiac arrhythmia, and auditory disturbance.

Accordingly, new psychopharmacological agents are needed which can solve these and other limitations and/or reach a larger cross-section of patients with neuropsychiatric pathology. Such neuropsychiatric pathology includes many difficult-to-treat mood, anxiety and personality disorders such as depression and PTSD, but also: fibromyalgia, suicidal ideation, substance use disorders (SUD), eating disorders, Borderline Personality Disorder (BPD) and other personality disorders, obsessive-compulsive disorder (OCD), palliative care/end-of-life anxiety, existential distress, chronic pain syndromes, body dysmorphia, phobias, social anxiety in autistic adults, and even sleep regulation.

SUMMARY OF THE INVENTION

In one aspect, provided herein are methods of treating and/or preventing a neuropsychiatric illness and/or ameliorating a symptom thereof in a subject in need thereof, comprising administering a therapeutically effective amount of methylone (3,4-methylenedioxy-N-methylcathinone) to the subject. In some embodiments, the methylone dose ranges from 0.8-5 mg/kg. In some embodiments, the methylone dose ranges from 0.8-30 mg/kg. In some embodiments, the methylone dose ranges from 50-350 mg. In some embodiments, the methylone dose ranges from 50-500 mg. In some embodiments, the methylone dose ranges from 50-1,000 mg. In some embodiments, an initial dose of methylone (e.g., 50-500 mg) is administered, which is then boosted 30 minutes-4 hours later by administering a second methylone dose (e.g., an additional 25-250 mg of methylone). In some embodiments, the methylone is administered, e.g., as a single dose or according to the foregoing dosing schedule, once a week or twice or more times per week (up to daily dosing) or two or three times a day. In some embodiments, the methylone is administered as an extended release or sustained release formulation, for example, to achieve a dosing regimen disclosed herein and releasing 50 mg to 1 g on a set schedule to patients according to the indication(s) being treated in those patients. In some embodiments, the subject is suicidal. In some embodiments, the neuropsychiatric illness is treatment-resistant. In some embodiments, the methylone is used in combination with an additional therapy for the neuropsychiatric illness. In some embodiments, the additional therapy is psychotherapy. In some embodiments, the additional therapy comprises administering one or more additional psychoactive agents to the subject. In some embodiments, the additional psychoactive agents are selected from the group consisting of selective-serotonin reuptake (SSRIs), tricyclic antidepressants (TCAs), monoamine oxidase inhibitors (MAOIs), serotonin-norepinephrine reuptake inhibitors (SNRIs), serotonin-norepinephrine-dopamine reuptake inhibitors (SDNRIs), and anxiolytic agents. In some embodiments, the neuropsychiatric illness is a Depressive Disorder. In some embodiments, the Depressive Disorder is selected from the group consisting of Disruptive Mood Dysregulation Disorder, Major Depressive Disorder, Single and Recurrent Episodes, Persistent Depressive Disorder (Dysthymia), Premenstrual Dysphoric Disorder, Substance/Medication-Induced Depressive Disorder, Depressive Disorder Due to Another Medical Condition, Other Specified Depressive Disorder, Unspecified Depressive Disorder, and combinations thereof. In some embodiments, the neuropsychiatric illness is post-traumatic stress disorder (PTSD). In some embodiments, the neuropsychiatric illness is acute stress disorder. In some embodiments, the neuropsychiatric illness is Fibromyalgia. In some embodiments, the neuropsychiatric illness is a mood disorder. In some embodiments, the neuropsychiatric illness is an anxiety disorder. In some embodiments, the neuropsychiatric illness is an eating disorder. In some embodiments, the neuropsychiatric illness is a Personality Disorder (PD). In some embodiments, the Personality Disorder is selected from the group consisting of Borderline Personality Disorder (BPD), Avoidant Personality Disorder (AvPD), Antisocial Personality Disorder (AsPD), Schizotypal Personality Disorder, Other Anxiety and Panic producing Disorders, Specific personality disorders, Impulse disorders, Gender identity disorders, Paraphilias, Other sexual disorders, Other disorders of adult personality and behavior, Unspecified disorder of adult personality and behavior, Personality and behavioral disorders due to known physiological conditions. In some embodiments, the subject with the PD also has a Depressive Disorder.

In another aspect, provided herein are methods of treating and/or preventing a neuropsychiatric illness and/or ameliorating a symptom thereof in a subject in need thereof, comprising: administering a therapeutically effective amount of 2C-B (4-Bromo-2,5-dimethoxyphenethylamine) to the subject. In some embodiments, the 2C-B dose ranges from 0.8-5 mg/kg. In some embodiments, the 2C-B dose ranges from 0.8-30 mg/kg. In some embodiments, the 2C-B dose ranges from 50-350 mg. In some embodiments, the 2C-B dose ranges from 50-500 mg. In some embodiments, the 2C-B dose ranges from 50-1,000 mg. In some embodiments, an initial dose of 2C-B is administered (e.g., 50-500 mg), which is then boosted 30 minutes-4 hours later by administering a second 2C-B dose (e.g., an additional 25-250 mg of 2C-B). In some embodiments, the 2C-B is administered, e.g., as a single dose or according to the foregoing dosing schedule, once a week or twice or more per week (up to daily dosing) or two or three times a day. In some embodiments, the 2C-B is administered as an extended release or sustained release formulation, for example, to achieve a dosing regimen disclosed herein and releasing 50 mg to 1 g on a set schedule to patients according to the indication(s) being treated in those patients. In some embodiments, the neuropsychiatric illness is a Somatic Symptom Disorders. In some embodiments, the Somatic Symptom Disorder is selected from the group consisting of Illness Anxiety Disorder, Conversion Disorder (Functional Neurological Symptom Disorder), Psychological Factors Affecting Other Medical Conditions, Factitious Disorder, Other Specified Somatic Symptom and Related Disorder, Unspecified Somatic Symptom and Related Disorder, and combinations thereof. In some embodiments, the neuropsychiatric illness is Fibromyalgia. In some embodiments, the neuropsychiatric illness is a Depressive Disorder. In some embodiments, the Depressive Disorder is selected from the group consisting of Disruptive Mood Dysregulation Disorder, Major Depressive Disorder, Single and Recurrent Episodes, Persistent Depressive Disorder (Dysthymia), Premenstrual Dysphoric Disorder, Substance/Medication-Induced Depressive Disorder, Depressive Disorder Due to Another Medical Condition, Other Specified Depressive Disorder, Unspecified Depressive Disorder, and combinations thereof. In some embodiments, the neuropsychiatric illness is post-traumatic stress disorder (PTSD). In some embodiments, the neuropsychiatric illness is acute stress disorder. In some embodiments, the neuropsychiatric illness is a mood disorder. In some embodiments, the neuropsychiatric illness is an anxiety disorder. In some embodiments, the neuropsychiatric illness is an eating disorder. In some embodiments, the subject is suicidal. In some embodiments, the neuropsychiatric illness is treatment-resistant. In some embodiments, the 2C-B is used in combination with an additional therapy for the neuropsychiatric illness. In some embodiments, the additional therapy is psychotherapy. In some embodiments, the additional therapy comprises administering one or more additional psychoactive agents to the subject. In some embodiments, the additional psychoactive agents are selected from the group consisting of SSRIs, TCAs, MAOIs, SNRIs, SDNRIs, and anxiolytics.

In another aspect, provided herein are methods of treating and/or preventing a neuropsychiatric illness and/or ameliorating a symptom thereof in a subject in need thereof, comprising: administering a therapeutically effective amount of MBDB (N-methyl-1-(1,3-benzodioxol-5-yl)-2-aminobutane) to the subject. In some embodiments, the MBDB dose ranges from 0.8-5 mg/kg. In some embodiments, the MBDB dose ranges from 0.8-30 mg/kg. In some embodiments, the MBDB dose ranges from 50-350 mg. In some embodiments, the MBDB dose ranges from 50-500 mg. In some embodiments, the MBDB dose ranges from 50-1,000 mg. In some embodiments, an initial dose of MBDB is administered (e.g., 50-500 mg), which is then boosted 30 minutes-4 hours later by administering a second MBDB dose, e.g., an additional 25-250 mg of MBDB. In some embodiments, the MBDB is administered, e.g., as a single dose or according to the foregoing dosing schedule, once a week or twice or more per week (up to daily dosing) or two or three times a day. In some embodiments, the MBDB is administered as an extended release or sustained release formulation, for example, to achieve a dosing regimen disclosed herein and releasing 50 mg to 1 g on a set schedule to patients according to the indication(s) being treated in those patients. In some embodiments, the neuropsychiatric illness is an Anxiety Disorder. In some embodiments, the Anxiety Disorder is selected from the group consisting of Generalized anxiety disorder, Panic disorder, Panic attack, Phobic anxiety disorders, Illness Anxiety Disorder, dissociative, stress-related, somatoform other nonpsychotic mental disorders, acute stress reaction, transient adjustment reaction, neurasthenia, psychophysiologic disorders, Obsessive-compulsive disorder, Reaction to severe stress and adjustment disorders, Separation Anxiety Disorder, episodic paroxysmal anxicty, Selective Mutism, Specific Phobia, Social Anxiety Disorder (Social Phobia), Agoraphobia, Substance/Medication-Induced Anxiety Disorder, Anxiety Disorder Due to Another Medical Condition, Anxiety in pregnancy and childbirth, Anxiety in pregnancy antepartum (before childbirth), Anxiety postpartum, Animal type phobia, Arachnophobia, Other animal type phobia, Natural environment type phobia, Fear of thunderstorms, Fear of blood, Fear of injections and transfusions, Fear of other medical care, Fear of injury, Situational type phobia, Claustrophobia, Acrophobia, Other Unspecified Anxiety Disorder, Body Dysmorphic Disorder Hoarding Disorder Trichotillomania (Hair-Pulling Disorder) Excoriation (Skin-Picking), and combinations thereof. In some embodiments, the subject is suicidal. In some embodiments, the neuropsychiatric illness is treatment-resistant. In some embodiments, the neuropsychiatric illness is post-traumatic stress disorder (PTSD). In some embodiments, the neuropsychiatric illness is acute stress disorder. In some embodiments, the neuropsychiatric illness is Fibromyalgia. In some embodiments, the MBDB is used in combination with an additional therapy for the neuropsychiatric illness. In some embodiments, the additional therapy is psychotherapy. In some embodiments, the additional therapy comprises administering one or more additional psychoactive agents to the subject. In some embodiments, the additional psychoactive agents are selected from the group consisting of SSRIs, TCAs, MAOIs, SNRIs, SDNRIs, and anxiolytics.

Other features and advantages of this invention will become apparent from the following detailed description examples and figures. It should be understood, however, that the detailed description and the specific examples while indicating preferred embodiments are given by way of illustration only, since various changes and modifications will become apparent to those skilled in the art from this detailed description.

BRIEF DESCRIPTION OF THE DRAWINGS

The following drawings form part of the present specification and are included to further demonstrate certain aspects of the present disclosure, the inventions of which can be better understood by reference to one or more of these drawings in combination with the detailed description of specific embodiments presented herein.

FIG. 2 shows the Baseline Disease Severity in Cohort 2 of Example 4.

FIGS. 5A-5C: Methylone has a robust antidepressant-like effect in the Forced Swim Test. Quantification of the time spent (FIG. 5A) immobile ($F_{(5, 34)}$=59.05, p<0.0001), (FIG. 5B) swimming ($F_{(5, 34)}$=28.72, p<0.0001) or (FIG. 5C) climbing ($F_{(5, 34)}$=3.195, p<0.05) during a 5-min rat Forced Swim Test. Rats were subjected to a 15 minute swim 24 h before testing. Fluoxetine (10 mg/kg, IP) was administered 1, 5, and 23.5 h before testing. Methylone (5, 15, 30 mg/kg, IP) was administered 30 min before testing. All data are presented as means+/−SEM. One-way ANOVA and post-hoc Tukey's test. *p<0.05 vs. vehicle 1× group; ****p<0.0001 vs. vehicle 1× group; ++++p<0.0001 vs. vehicle 3× group; N=6-8 per group.

FIGS. 7A-7C: 2C-B has a fast-acting antidepressant-like effect in the Forced Swim Test. Quantification of the time spent (FIG. 7A) immobile ($F_{(5, 34)}$=17.73, p<0.0001), (FIG. 7B) swimming ($F_{(5, 34)}$=16.49, p<0.0001) or (FIG. 7C) climbing ($F_{(5, 34)}$=4.984, p<0.001) during a 5-min rat Forced Swim Test. Rats were subjected to a 15 minute swim 24 h before testing. Fluoxetine (10 mg/kg, IP) was administered 1, 5, and 23.5 h before testing. 2C-B (2.5, 10, 20 mg/kg, IP) was administered 30 min before testing. All data are presented as means+/−SEM. One-way ANOVA and post-hoc Tukey's test. p<0.01 vs. vehicle 1× group; **p<0.0001 vs. vehicle 1× group; ++++p<0.0001 vs. vehicle 3× group; +++p<0.001 vs. vehicle 3× group N=6-8 per group.

(FIG. 8A) Schematic of experimental design. Quantification of the time spent (FIG. 8B) immobile ($F_{(4,31)}$=17.05, p<0.0001), (FIG. 8C) climbing $F_{(4,31)}$=5.786, p<0.01) or (FIG. 8D) swimming ($F_{(4,31)}$=6.063, p<0.01) during a 5-min rat Forced Swim Test. Rats were subjected to a 15 minute swim 24 h before testing. Fluoxetine (10 mg/kg, IP) was administered 1, 5, and 23.5 h before testing. Methylone (5 or 15 mg/kg, IP) was administered 30 min before testing. All data are presented as means+/−SEM. *p<0.05, p<0.01, *p<0.001, ****p<0.0001 vs. Vehicle control group; +p<0.05, ++p<0.01 vs. Fluoxetine-treated group; $^a$p=0.06 vs. Fluoxetine-treated group; $^b$p=0.08 vs. Vehicle control group. N=6-8 per group.

(FIG. 9A) Schematic of experimental design. A single CS-US (tone-shock) pairing on day 1 was followed by 6 CS presentations in a novel context (context B). Methylone or saline vehicle was injected 30 min prior to extinction training on day 2. On day 3, the time spent freezing to the CS was quantified. (FIG. 9B) Freezing time during the first cue on day 3 (extinction recall) was significantly reduced by methylone compared to saline ($t_{(26)}$=2.350, p<0.05). (FIG. 9C) No locomotor changes were observed on day 3 ($t_{(26)}$=1.073, p>0.05). Data are mean+/−SEM. N=12 for methylone group (30 mg/kg, IP) and N=16 for saline control group. *p<0.05.

(FIG. 10A) Freezing time during the first extinction training trial on day 2 was significantly reduced by MBDB compared to saline controls (t(24)=3.095, p<0.01). (FIG. 10B) A small but significant increase in locomotor activity was also induced by MBDB on day 2 (t(24)=2.874, p<0.01). Data are mean+/−SEM. N=10 for MBDB group (5 mg/kg, IP) and N=16 for saline control group. **p<0.01 vs. vehicle control group.

(FIG. 11A) Time spent in the center revealed an anti-anxiety effect of methylone compared to vehicle treated controls ($F_{(3, 20)}$=7.139, p<0.01). (FIG. 11B) Total distance traveled showed increased locomotion following mid- and high doses of methylone ($F_{(3,20)}$=6.209, p<0.01). Data are mean+/−SEM. N=6 per group. *p<0.05; **p<0.01 vs. vehicle control group.

DETAILED DESCRIPTION OF THE INVENTION

Figure 1:
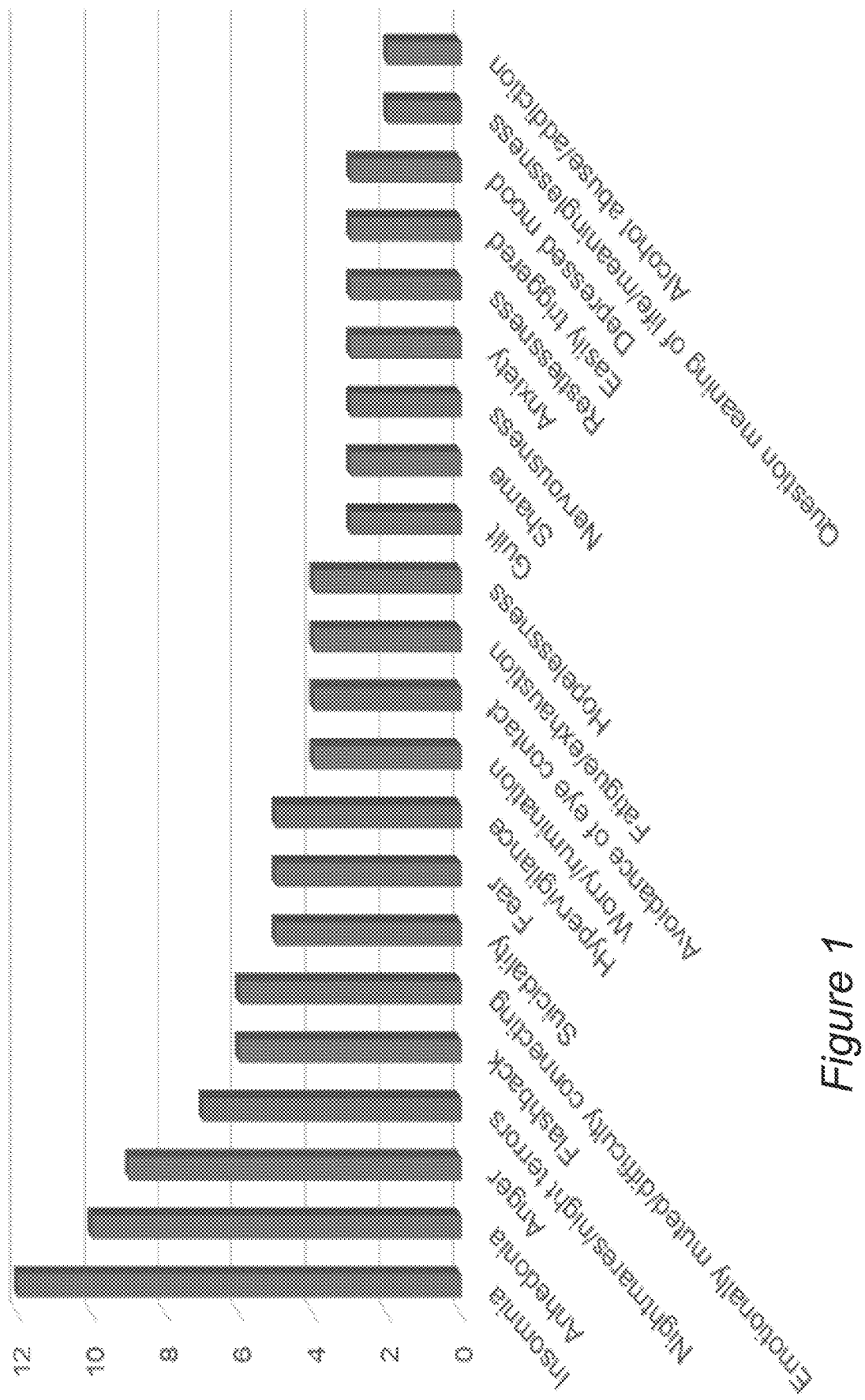
FIG. 1 shows the baseline symptom inventory for symptoms occurring in 2 or more of the 28 patients included in Cohort 2 of Example 4.

The present inventors identify methylone as a suitable agent for the treatment of CNS disorders. Methylone (3,4-methylenedioxy-N-methylcathinone; also known as "βk-MDMA") is a synthetic empathogenic cathinone and a close structural analogue of MDMA, but with a >50% shorter half-life. There are no FDA-registered clinical trials of its efficacy or safety profile, after its placement into Schedule I restricted status by the United States DEA in 2010. Methylone and MDMA resemble amphetamines and are agonists of the 5-HT$_2$ family of serotonin receptors. In vitro release assays using rat brain synaptosomes reveal that methylone is a nonselective substrate for plasma membrane monoamine transporters and receptors.

Methylone acts as a mixed reuptake inhibitor/releasing agent, and by comparison to MDMA, has 3× lower affinity for the serotonin transporter, but similar affinity for the norepinephrine and dopamine transporters. This reduced serotonergic pathway predominance is one reason why its efficacy as an antidepressant is not expected. In addition, the "comedown" effects from amphetamines, including MDMA or synthetic cathinones like methylone, include intense depression and fatigue. Methylone produced a widespread depletion of 5-HT and the serotonin transporter 5-HTT levels in rats that resembles a depressed neurological state. Depression has also been reported in humans using methylone. Other adverse effects include anxiety, anorexia, derealization/depersonalization, impaired short-term memory, psychosis, hallucinations, suicidal ideations, irritability, motivation suppression, thought deceleration, wakefulness, involuntary tremors, bruxism, jaw clenching, trismus, and unsteadiness of the hands and gait.

Taken together, the animal and human data do not point to a potential medical use for methylone as a treatment for CNS disorders, including depression and PTSD. It is unexpected that methylone—with low(est) 5-HT agonism in its class of synthetic cathinones—would be useful for the indications identified by the present inventors in patients with non-response, treatment-resistance, contraindications, or objections to current standard of care. This would include methylone administration either alone or in combination with an SSRI, TCA, MAOI, SNRI, SDNRI, or anxiolytics such as benzodiazepines, β-blockers, alpha-blockers, and buspirone.

The present inventors find that methylone has mainstream potential as a CNS medication, including as an antidepressant or as a treatment for PTSD, or as an anxiolytic. As compared to other treatments, methylone has advantages over current therapies and others in development: better efficacy to safety ratio, faster-acting effect profile, fewer drug-drug interactions, more effective combination therapy, more frequent adjunct in individual or group psychotherapy. Methylone also causes fewer side effects after longer sessions or chronic usage, unlike symptoms of SSRI tolerance as efficacy wears off for a large proportion of patients. Symptoms of SSRI tolerance include fatigue, loss of motivation, weariness, sleep disorders, restless leg syndrome, irritability, and depressive moods.

The present inventors further identify 2C-B (2,5-dimethoxy-4-bromophenethylamine), as a suitable agent to treat and provide symptom relief in Somatic Symptom Disorders (SSD), Depressive Disorders, PTSD, and other Central Nervous System (CNS) diseases—but especially Fibromyalgia, a syndrome of widespread musculoskeletal pain accompanied by fatigue, sleep, memory and mood disorder symptoms. Treatments for fibromyalgia, such as the SNRIs duloxetine and milnacipran, are often outweighed by their potential harms, and only a minority of fibromyalgia patients might experience substantial symptom relief without adverse events.

2C-B is a psychoactive phenethylamine reported to have limited efficacy as a $5-HT_{2A}$ receptor partial agonist, yet we postulate that it is useful in $5-HT_{2A}$ implicated pathophysiology. In vitro and in vivo models suggest it acts as a mixed $5-HT_{2A}$ antagonist, and a $5-HT_{2B}$ and $5-HT_{2C}$ partial agonist—receptors which are particularly expressed on apical dendrites of neocortical pyramidal cells in layer V. It is a Schedule 1 drug due to its unfavorable characteristics and potential for abuse, as numerous hospitalizations have been tied to 2C-B ingestion via toxicology studies.

Human Open-Label Studies in experienced drug users who self-administered 2C-B, varying in dose from 10 to 20 mg, found no serious adverse effects. At doses higher than 20 mg, 2C-B users report more euphoria, kaleidoscope vision, and distorted perception.

Chronic psychiatric disorders often share a common core of intractable symptoms that respond favorably to psychoactive medicines, via complex pharmacological effects that may be further modulated by psychotherapy. Patients experience multiple co-occurring symptoms that are related to each other, have independent or concurrent temporal dimensions or gradings of severity, and may have shared underlying mechanisms. Clusters can also be considered "symptom endophenotypes" which cut across syndromes and disorders via neurobiological correlates of brain circuits and neurotransmitters.

Without wishing to be bound by theory, the inventors hypothesize that 2C-B—via an acute, somatically-transformative phenomenology and durable psychoactive pharmacological and physiological effect profile—has a compelling neurobiological rationale to treat SSD, depression, anxiety, PTSD and comorbid conditions. SSDs including Fibromyalgia are often diagnoses of exclusion, with chronic somatic symptoms of indeterminate biological or medical cause. The named entities in the DSM-5 under SSD are illness anxiety disorder/hypochondriasis, functional neurological/conversion disorder, pain disorder (under which fibromyalgia is classified), body dysmorphic disorder, and somatoform disorder "not otherwise specified." They are often comorbid with Mood & Affective disorders, which can include a mood disturbance cluster, and a neuropsychological discomfort cluster. Fibromyalgia patients can be successfully treated with 2C-B at a lower dose range from 1-24 mg, and in combination with other psychoactive medications for CNS disorders.

The present inventors further identify MBDB (N-methyl-1-(1,3-benzodioxol-5-yl)-2-aminobutane) as a suitable agent to treat and provide symptom relief in a wide range of Anxiety Disorders, or as an antidepressant. Animal and human data do not point to a potential medical use for MBDB as a treatment for CNS disorders, or otherwise. Experimental drug users who self-administered MBDB under supervision in a controlled setting, varying in dose from 100 to 300 mg, found no serious adverse effects. In summary, MBDB can be used as an anxiolytic, and this treatment effect can be reliably evaluated using measures such as the GAD-7 or the Generalized Anxiety Disorder Severity Scale (GADSS).

Diseases, conditions, and disorders listed herein are described in the Diagnostic and Statistical Manual of Mental Disorders (DSM-5), published by the American Psychiatric Association, or in International Classification of Diseases (ICD), published by the World Health Organization.

A psychiatric illness, condition, disease or disorder includes, without limitation, the following, and all intermediate ICD-10 codes in the ranges defined:

F01-F09 Mental Disorders Due to Known Physiological Conditions

F01 Vascular dementia; F02 Dementia in other diseases classified elsewhere; F03 Unspecified dementia; F04 Amnestic disorder due to known physiological condition; F05 Delirium due to known physiological condition; F06 Other mental disorders due to known physiological condition; F07 Personality and behavioral disorders due to known physiological condition; F09 Unspecified mental disorder due to known physiological condition.

F10-F19 Mental and Behavioral Disorders Due to Psychoactive Substance Use

F10 Alcohol related disorders; F11 Opioid related disorders; F12 Cannabis related disorders; F13 Sedative, hypnotic, or anxiolytic related disorders; F14 Cocaine related disorders; F15 Other stimulant related disorders; F16 Hallucinogen related disorders; F17 Nicotine dependence; F18 Inhalant related disorders; F19 Other psychoactive substance related disorders. Caffeine-Related Disorders Caffeine Intoxication Caffeine Withdrawal Other Caffeine-Induced Disorders Substance-Related Disorder Non-Substance-Related Disorders Gambling Disorder Neurocognitive Disorders Delirium Other Specified Delirium Unspecified Delirium Major and Mild Neurocognitive Disorders Major Neurocognitive Disorder Mild Neurocognitive Disorder Major or Mild Neurocognitive Disorder Due to Alzheimer's Disease Major or Mild Frontotemporal Neurocognitive Disorder Major or Mild Neurocognitive Disorder With Lewy Bodies Major or Mild Vascular Neurocognitive Disorder Major or Mild Neurocognitive Disorder Due to Traumatic Brain Injury Substance/Medication-Induced Major or Mild Neurocognitive Disorder Major or Mild Neurocognitive Disorder Due to HIV Infection Major or Mild Neurocognitive Disorder Due to Prion Disease Major or Mild Neurocognitive Disorder Due to Parkinson's Disease Major or Mild Neurocognitive Disorder Due to Huntington's Disease Major or Mild Neurocognitive Disorder Due to Another Medical Condition Major or Mild Neurocognitive Disorder Due to Multiple Etiologies Unspecified Neurocognitive Disorder.

F20-F29 Schizophrenia, Schizotypal, Delusional, and Other Non-Mood Psychotic Disorders F20 Schizophrenia; F21 Schizotypal disorder; F22 Delusional disorders; F23 Brief psychotic disorder; F24 Shared psychotic disorder; F25 Schizoaffective disorders; F28 Other psychotic disorder not due to a substance or known physiological condition; F29 Unspecified psychosis not due to a substance or known physiological condition.

F30-F39 Mood [Affective] Disorders

F30 Manic episode; F31 Bipolar disorder; F32 Major depressive disorder, single episode; F33 Major depressive disorder, recurrent; F34 Persistent mood [affective] disorders; F39 Unspecified mood [affective] disorder.

Disruptive Mood Dysregulation Disorder, Persistent Depressive Disorder (Dysthymia) Premenstrual Dysphoric Disorder Substance/Medication-Induced Depressive Disorder Depressive Disorder Due to Another Medical Condition Other Specified Depressive Disorder Unspecified Depressive Disorder, Treatment-resistant depression.

F40-F48 Anxiety, Dissociative, Stress-Related, Somatoform other Nonpsychotic Mental Disorders F40 Phobic anxiety disorders; F41 Other anxiety disorders; F42 Obsessive-compulsive disorder; F43 Reaction to severe stress, and adjustment disorders; F44 Dissociative and conversion disorders; F45 Somatoform disorders; F48 Other nonpsychotic mental disorders.

Anxiety Disorders: Separation Anxiety Disorder Selective Mutism Specific Phobia Social Anxiety Disorder (Social Phobia) Panic Disorder Panic Attack (Specifier) Agoraphobia Generalized Anxiety Disorder Substance/Medication-Induced Anxiety Disorder Anxiety Disorder Due to Another Medical Condition Other Specified Anxiety Disorder Obsessive-Compulsive Disorder Body Dysmorphic Disorder Hoarding Disorder Trichotillomania (Hair-Pulling Disorder) Excoriation (Skin-Picking) Disorder Substance/Medication-Induced Obsessive-Compulsive and Related Disorder Obsessive-Compulsive and Related Disorder Due to Another Medical Condition Other Specified Obsessive-Compulsive and Related Disorder Unspecified Trauma- and Stressor-Related Disorders: Reactive Attachment Disorder Disinhibited Social Engagement Disorder Posttraumatic Stress Disorder Acute Stress Disorder Adjustment Disorders Other Specified Trauma- and Stressor-Related Disorder Unspecified Trauma- and Stressor-Related Disorder Somatic Symptom and Related Disorders: Somatic Symptom Disorder Illness Anxiety Disorder Conversion Disorder (Functional Neurological Symptom Disorder) Psychological Factors Affecting Other Medical Conditions Factitious Disorder Other Specified Somatic Symptom and Related Disorder Unspecified Somatic Symptom and Related Disorder Feeding and Eating Disorders: Pica Rumination Disorder Avoidant/Restrictive Food Intake Disorder Anorexia Nervosa Bulimia Nervosa Binge-Eating Disorder Other Specified Feeding or Eating Disorder Unspecified Feeding or Eating Disorder Sleep-Wake Disorders: Insomnia Disorder Hypersomnolence Disorder Narcolepsy Breathing-Related Sleep Disorders Obstructive Sleep Apnea Hypopnea Central Sleep Apnea Sleep-Related Hypoventilation Circadian Rhythm Sleep-Wake Disorders Parasomnias Non-Rapid Eye Movement Sleep Arousal Disorders Sleepwalking Sleep Terrors Nightmare Disorder Rapid Eye Movement Sleep Behavior Disorder Restless Legs Syndrome Substance/Medication-Induced Sleep Disorder Other Specified Insomnia Disorder Unspecified Insomnia Disorder Other Specified Hypersomnolence Disorder Unspecified Hypersomnolence Disorder Other Specified Sleep-Wake Disorder Unspecified Sleep-Wake Disorder Sexual Dysfunctions: Delayed Ejaculation Erectile Disorder Female Orgasmic Disorder Female Sexual Interest/Arousal Disorder Genito-Pelvic Pain/Penetration Disorder Male Hypoactive Sexual Desire Disorder Premature (Early) Ejaculation Substance/Medication-Induced Sexual Dysfunction Other Specified Sexual Dysfunction Unspecified Sexual Dysfunction Gender Dysphoria Gender Dysphoria Other Specified Gender Dysphoria Unspecified Gender Dysphoria F50-F59 Behavioral Syndromes Associated with Physiological Disturbances and Physical Factors F50 Eating disorders; F51 Sleep disorders not due to a substance or known physiological condition; F52 Sexual dysfunction not due to a substance or known physiological condition; F53 Mental and behavioral disorders associated with the puerperium, not elsewhere classified; F54 Psychological and behavioral factors associated with disorders or diseases classified elsewhere; F55 Abuse of non-psychoactive substances; F59 Unspecified behavioral syndromes associated with physiological disturbances and physical.

F60-F69 Disorders of Adult Personality and Behavior

F60 Specific personality disorders; F63 Impulse disorders; F64 Gender identity disorders; F65 Paraphilias; F66 Other sexual disorders; F68 Other disorders of adult personality and behavior; F69 Unspecified disorder of adult personality and behavior.

Disruptive, Impulse-Control, and Conduct Disorders: Oppositional Defiant Disorder Intermittent Explosive Disorder Conduct Disorder Antisocial Personality Disorder Pyromania Kleptomania Other Specified Disruptive, Impulse-Control, and Conduct Disorder Unspecified Disruptive, Impulse-Control, and Conduct Disorder Personality Disorders General Personality Disorder Cluster A Personality Disorders Paranoid Personality Disorder Schizoid Personality Disorder Schizotypal Personality Disorder Cluster B Personality Disorders Antisocial Personality Disorder Borderline Personality Disorder Histrionic Personality Disorder Narcissistic Personality Disorder Cluster C Personality Disorders Avoidant Personality Disorder Dependent Personality Disorder Obsessive-Compulsive Personality Disorder Other Personality Disorders Personality Change Due to Another Medical Condition Other Specified Personality Disorder Unspecified Personality Disorder Conditions for Further Study Attenuated Psychosis Syndrome Depressive Episodes With Short-Duration Hypomania Persistent Complex Bereavement Disorder Gaming Disorder Neurobehavioral Disorder Associated With Prenatal Alcohol Exposure Suicidal Behavior Disorder Nonsuicidal Self-Injury F70-F79 Intellectual Disabilities F70 Mild intellectual disabilities; F71 Moderate intellectual disabilities; F72 Severe intellectual disabilities; F73 Profound intellectual disabilities; F78 Other intellectual disabilities; F79 Unspecified intellectual disabilities F80-F89 Pervasive and Specific Developmental Disorders F80 Specific developmental disorders of speech and language; F81 Specific developmental disorders of scholastic skills; F82 Specific developmental disorder of motor function; F84 Pervasive developmental disorders; F88 Other disorders of psychological development; F89 Unspecified disorder of psychological development. Neurodevelopmental Disorders Intellectual Disabilities Intellectual Disability (Intellectual Developmental Disorder) Global Developmental Delay Unspecified Intellectual Disability (Intellectual Developmental Disorder) Communication Disorders Language Disorder Speech Sound Disorder (previously Phonological Disorder) Childhood-Onset Fluency Disorder (Stuttering) Social (Pragmatic) Communication Disorder Unspecified Communication Disorder Autism Spectrum Disorder Autism Spectrum Disorder Attention-Deficit/Hyperactivity Disorder Attention-Deficit/Hyperactivity Disorder Other Specified Attention-Deficit/Hyperactivity Disorder Unspecified Attention-Deficit/Hyperactivity Disorder Specific Learning Disorder Specific Learning Disorder Motor Disorders Developmental Coordination Disorder Stereotypic Movement Disorder Tic Disorders Tourette's Disorder Persistent (Chronic) Motor or Vocal Tic Disorder Provisional Tic Disorder Other Specified Tic Disorder Unspecified Tic Disorder Other Neurodevelopmental Disorders Other Specified Neurodevelopmental Disorder Unspecified Neurodevelopmental Disorder F90-F98 Behavioral and Emotional Disorders with Onset Usually Occurring in Childhood and Adolescence.

F90 Attention-deficit hyperactivity disorders; F91 Conduct disorders; F93 Emotional disorders with onset specific to childhood; F94 Disorders of social functioning with onset specific to childhood and adolescence; F95 Tic disorder; F98 Other behavioral and emotional disorders with onset usually occurring in childhood and adolescence.

As used herein, a neurologic illness, condition, disease or disorder includes, without limitation, the following, and all intermediate ICD-10 codes in the ranges defined:

G00-G09 Inflammatory Diseases of the Central Nervous System

G00 Bacterial meningitis, not elsewhere classified; G01 Meningitis in bacterial diseases classified elsewhere; G02 Meningitis in other infectious and parasitic diseases classified elsewhere; G03 Meningitis due to other and unspecified causes; G04 Encephalitis, myelitis and encephalomyelitis; G05 Encephalitis, myelitis and encephalomyelitis in diseases classified elsewhere; G06 Intracranial and intraspinal abscess and granuloma; G07 Intracranial and intraspinal abscess and granuloma in diseases classified elsewhere; G08 Intracranial and intraspinal phlebitis and thrombophlebitis; G09 Sequelae of inflammatory diseases of central nervous system. Adding the exclusions: certain conditions originating in the perinatal period (P04-P96) certain infectious and parasitic diseases (A00-B99) complications of pregnancy, childbirth and the puerperium (O00-O9A) congenital malformations, deformations, and chromosomal abnormalities (Q00-Q99) endocrine, nutritional and metabolic diseases (E00-E88) injury, poisoning and certain other consequences of external causes (S00-T88) neoplasms (C00-D49) symptoms, signs and abnormal clinical and laboratory findings, not elsewhere classified (R00-R94).

G10-G14 Systemic Atrophies Primarily Affecting the Central Nervous System

G10 Huntington's disease; G11 Hereditary ataxia; G12 Spinal muscular atrophy and related syndromes; G13 Systemic atrophies primarily affecting central nervous system in diseases classified elsewhere; G14 Postpolio syndrome G20-G26 Extrapyramidal and Movement Disorders G20 Parkinson's disease; G21 Secondary parkinsonism; G23 Other degenerative diseases of basal ganglia; G24 Dystonia; G25 Other extrapyramidal and movement disorders; G26 Extrapyramidal and movement disorders in diseases classified elsewhere G30-G32 Other Degenerative Diseases of the Nervous System G30 Alzheimer's disease; G31 Other degenerative diseases of nervous system, not elsewhere classified; G32 Other degenerative disorders of nervous system in diseases classified elsewhere G35-G37 Demyelinating Diseases of the Central Nervous System G35 Multiple sclerosis; G36 Other acute disseminated demyelination; G37 Other demyelinating diseases of central nervous system G40-G47 Episodic and Paroxysmal Disorders G40 Epilepsy and recurrent seizures; G43 Migraine; G44 Other headache syndromes; G45 Transient cerebral ischemic attacks and related syndromes; G46 Vascular syndromes of brain in cerebrovascular diseases; G47 Sleep disorders G50-G59 Nerve, Nerve Root and Plexus Disorders G50 Disorders of trigeminal nerve; G51 Facial nerve disorders; G52 Disorders of other cranial nerves; G53 Cranial nerve disorders in diseases classified elsewhere; G54 Nerve root and plexus disorders; G55 Nerve root and plexus compressions in diseases classified elsewhere; G56 Mononeuropathies of upper limb; G57 Mononeuropathies of lower limb; G58 Other mononeuropathies; G59 Mononeuropathy in diseases classified elsewhere. Adding the exclusions: current traumatic nerve, nerve root and plexus disorders, nerve by body region neuralgia NOS (M79.2) neuritis NOS (M79.2), peripheral neuritis in pregnancy (O26.82), radiculitis NOS (M54.1)

G60-G65 Polyneuropathies and Other Disorders of the Peripheral Nervous System

G60 Hereditary and idiopathic neuropathy; G61 Inflammatory polyneuropathy; G62 Other and unspecified polyneuropathies; G63 Polyneuropathy in diseases classified elsewhere; G64 Other disorders of peripheral nervous system; G65 Sequelae of inflammatory and toxic polyneuropathies G70-G73 Diseases of Myoneural Junction and Muscle G70 Myasthenia gravis and other myoneural disorders; G71 Primary disorders of muscles; G72 Other and unspecified myopathies; G73 Disorders of myoneural junction and muscle in diseases classified elsewhere G80-G83 Cerebral Palsy and Other Paralytic Syndromes G80 Cerebral palsy; G81 Hemiplegia and hemiparesis; G82 Paraplegia (paraparesis) and quadriplegia (quadriparesis); G83 Other paralytic syndromes.

G89-G99 Other Disorders of the Nervous System

G89 Pain, not elsewhere classified; G90 Disorders of autonomic nervous system; G91 Hydrocephalus; G92 Toxic encephalopathy; G93 Other disorders of brain; G94 Other disorders of brain in diseases classified elsewhere; G95 Other and unspecified diseases of spinal cord; G96 Other disorders of central nervous system; G97 Intraoperative and postprocedural complications and disorders of nervous system, not elsewhere classified; G98 Other disorders of nervous system not elsewhere classified; G99 Other disorders of nervous system in diseases classified elsewhere.

As used herein, "treatment resistant depression" (TRD) is a shorthand signifier for all related terms, approaches to management, etc., defined here as including but not limited to: non-responder depression, treatment refractory depression, partial response depression, optimization strategy, switching strategy, combination strategy, augmentation strategy, bupropione, mirtazapine, mianserine, lithium, thyroid hormones, second generation antipsychotics (SGA), dopamine agonists, lamotrigine, psychostimulants, dextromethorphan, dextrorphan, ketamine, omega-3 fatty acids, pindolol, sex steroids, and glucocorticoid agents. Approaches to management include treatment strategies such as: (1) switching from an ineffective antidepressant to a new antidepressant from a similar or different class; (2) combining a current antidepressant regimen with a second antidepressant from a different class; and (3) augmenting a current antidepressant regimen with a second agent not thought to be an antidepressant itself.

As used herein, the terms "reduce," "decrease," "lessen" and similar terms mean a decrease of at least about 10%, about 15%, about 20%, about 25%, about 35%, about 50%, about 75%, about 80%, about 85%, about 90%, about 95%, about 97%, or more.

As used herein, the terms "improve," "increase," "enhance," and similar terms indicate an increase of at least about 10%, about 15%, about 20%, about 25%, about 50%, about 75%, about 100%, about 150%, about 200%, about 300%, about 400%, about 500%, or more.

As used herein, the terms "binds" or "binding" or grammatical equivalents, refer to compositions having affinity for each other. "Specific binding" is where the binding is selective between two molecules. A particular example of specific binding is that which occurs between an antibody and an antigen. Typically, specific binding can be distinguished from non-specific when the dissociation constant (KD) is less than about $1 \times 10^{-5}$ M or less than about $1 \times 10^{-6}$ M or $1 \times 10^{-7}$ M. Specific binding can be detected, for example, by ELISA, immunoprecipitation, coprecipitation, with or without chemical crosslinking, two-hybrid assays and the like. Appropriate controls can be used to distinguish between "specific" and "non-specific" binding.

In one embodiment, a variety of other therapeutic agents may find use for administration with the compositions and methods provided herein The psychoactive compounds provided herein may be used for various therapeutic purposes. In one embodiment, the compounds are administered to a subject to treat a neuropsychiatric illness. A "subject" for the purposes of the compositions and methods provided herein includes humans and other animals, preferably mammals and most preferably humans. Thus, the compounds provided herein have both human therapy and veterinary applications. In another embodiment the subject is a mammal, and in yet another embodiment the subject is human. By "condition" or "disease" herein are meant a disorder that may be ameliorated by the administration of a pharmaceutical composition comprising the compounds provided herein.

Methods and compositions described herein can be used for prophylaxis, as well as amelioration of signs and/or symptoms of a neuropsychiatric illness. The terms "treating" and "treatment" used to refer to treatment of a neuropsychiatric illness in a subject include: preventing, inhibiting or ameliorating the neuropsychiatric illness in the subject, as well as reducing or ameliorating a sign or symptom of the neuropsychiatric illness. Treatment goals may incorporate endpoints such as improvement in DSM-5 severity scales, to measure if resilience and quality of life are enhanced, with engagement of positive cognitive valence systems, and corresponding reduction in negative valence.

It is to be understood by one of skill in the art that the methods of treatment and/or prevention comprising administering a psychoactive compound provided herein for the treatment and/or prevention of one or more indications as described herein also include: the use of a psychoactive compound provided herein in the manufacture of a medicament for the treatment and/or prevention of one or more indications as described herein; and the use of a psychoactive compound provided herein for the treatment and/or prevention of one or more indications as described herein.

In some embodiments, a method of treating and/or preventing a neuropsychiatric illness and/or ameliorating a symptom thereof in a subject in need thereof comprises administering to the subject a therapeutically effective dose of a psychoactive compound provided herein. In some embodiments, a method of treating and/or preventing a neuropsychiatric illness and/or ameliorating a symptom thereof in a subject in need thereof comprises administering to the subject a therapeutically effective dose of a psychoactive compound provided herein in a controlled environment, wherein the subject is provided with psychological support.

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviations, per practice in the art. Alternatively, when referring to a measurable value such as an amount, a temporal duration, a concentration, and the like, may encompass variations of ±20% or ±10%, more preferably ±5%, even more preferably ±1% or ±0.5%, and still more preferably ±0.1% from the specified value, as such variations are appropriate to perform the disclosed methods.

Pharmaceutical compositions are contemplated for the psychoactive compounds and methods provided herein. Formulations of the compositions and methods provided herein are prepared for storage by mixing said compound having the desired degree of purity with optional pharmaceutically acceptable carriers, excipients or stabilizers, in the form of lyophilized formulations or aqueous solutions. Acceptable carriers, excipients, or stabilizers are nontoxic to recipients at the dosages and concentrations employed, and include buffers such as phosphate, citrate, acetate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; sweeteners and other flavoring agents; fillers such as microcrystalline cellulose, lactose, corn and other starches; binding agents; additives; coloring agents; salt-forming counter-ions such as sodium; metal complexes (e.g., Zn-protein complexes); and/ or non-ionic surfactants or polyethylene glycol (PEG). In another embodiment, the pharmaceutical compositions provided herein are in a water-soluble form, such as being present as pharmaceutically acceptable salts, which is meant to include both acid and base addition salts. "Pharmaceutically acceptable acid addition salt" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like. "Pharmaceutically acceptable base addition salts" include those derived from inorganic bases such as sodium, potassium, lithium, ammonium, calcium, magnesium, iron, zinc, copper, manganese, aluminum salts and the like. Particularly preferred are the ammonium, potassium, sodium, calcium, and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, and ethanolamine. The formulations to be used for in vivo administration are preferably sterile. This is readily accomplished by filtration through sterile filtration membranes or other methods.

Pharmaceutically acceptable excipients for formulations of psychoactive compounds provided herein include, but are not limited to: diluents, e.g., microcrystalline cellulose, starch, mannitol, calcium hydrogen phosphate anhydrous or co-mixtures of silicon dioxide, calcium carbonate, microcrystalline cellulose and talc; disintegrants, e.g., sodium starch glycolate or croscarmellose sodium; binders, e.g., povidone, co-povidone or hydroxyl propyl cellulose; lubricants, e.g., magnesium stearate or sodium stearyl fumurate; glidants, e.g., colloidal silicon dioxide; and film coats, e.g., Opadry II white or PVA based brown Opadry II.

The psychoactive compounds provided herein may also be entrapped in microcapsules prepared by methods including, but not limited to, coacervation techniques, interfacial polymerization (e.g., using hydroxymethylcellulose or gelatin-microcapsules, or poly-(methylmethacylate) microcapsules), colloidal drug delivery systems (e.g., liposomes, albumin microspheres, microemulsions, nano-particles and nano-capsules), and macroemulsions. Sustained-release preparations may be prepared. Suitable examples of sustained-release preparations include semipermeable matrices of solid hydrophobic polymer, which matrices are in the form of shaped articles, e.g., films, or microcapsules. Examples of sustained-release matrices include polyesters, hydrogels (for example poly(2-hydroxyethyl-methacrylate), or poly(vinylalcohol)), polylactides, copolymers of L-glutamic acid and gamma ethyl-L-glutamate, non-degradable ethylene-vinyl acetate, degradable lactic acid-glycolic acid copolymers (which are injectable microspheres composed of lactic acid-glycolic acid copolymer and leuprolide acetate), and poly-D-(−)-3-hydroxybutyric acid) which is a microsphere-based delivery system composed of the desired bioactive molecule incorporated into a matrix of poly-DL-lactide-co-glycolide (PLG).

Administration of the pharmaceutical composition comprising the psychoactives provided herein, preferably in the form of a sterile aqueous solution, may be done in a variety of ways, including, but not limited to orally, subcutaneously, intravenously, intranasally, intraotically, transdermally, topically (e.g., gels, salves, lotions, creams, etc.), intraperitoneally, intramuscularly, intrapulmonary, vaginally, parenterally, rectally, or intraocularly. As is known in the art, the pharmaceutical composition may be formulated accordingly depending upon the manner of introduction.

In some embodiments, the pharmaceutical formulation is an oral dosage form. In some embodiments, the pharmaceutical formulation is a parenteral dosage form. In some embodiments, the pharmaceutical composition comprises a tablet. In some embodiments, the pharmaceutical composition comprises a capsule. In some embodiments, the pharmaceutical composition comprises a dry powder. In some embodiments, the pharmaceutical composition comprises a solution. In some embodiments, more than one dosage form is administered to the subject at substantially the same time. In some embodiments, the subject may be administered the entire therapeutic dose in one tablet or capsule. In some embodiments, the therapeutic dose may be split among multiple tablets or capsules.

In some embodiments, a dose of a psychoactive compound provided herein may be in the range of about 1 mg to about 100 mg. For example, the dose may be about 1 mg, about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, or about 100 mg. In some embodiments, the dose of a psychoactive compound provided herein is between about 0.1 mg to about 100 mg, about 1 mg to about 50 mg, or about 5 mg to about 30 mg. In some embodiments, the dose of a psychoactive compound provided herein is about 1 mg, about 10 mg, or about 25 mg. In some embodiments, the dose of a psychoactive compound provided herein is in the range of about 0.001 mg to about 1 g. In some embodiments, the dose of a psychoactive compound provided herein is in the rage of about 100 mg to about 250 mg. In some embodiments, the dose of a psychoactive compound provided herein is about 25 mg.

In some embodiments, the psychoactive compound provided herein is administered daily. In some embodiments, the psychoactive compound is administered twice a day. In some embodiments, the psychoactive compound is administered three times a day. In some embodiments, the psychoactive compound is administered every other day. In some embodiments, the psychoactive compound is administered every third day. In some embodiments, the psychoactive compound is administered every fourth day. In some embodiments, the psychoactive compound is administered every fifth day. In some embodiments, the psychoactive compound is administered weekly. In some embodiments, the psychoactive compound is administered every other week. In some embodiments, the psychoactive compound is administered every third week. In some embodiments, the psychoactive compound is administered monthly.

In some embodiments, about 50 mg of the psychoactive compound is administered daily. In some embodiments, about 50 mg of the psychoactive compound is administered twice a day. In some embodiments, about 50 mg of the psychoactive compound is administered three times a day. In some embodiments, about 50 mg of the psychoactive compound is administered every other day. In some embodiments, about 50 mg of the psychoactive compound is administered every third day. In some embodiments, about 50 mg of the psychoactive compound is administered every fourth day. In some embodiments, about 50 mg of the psychoactive compound is administered every fifth day. In some embodiments, about 50 mg of the psychoactive compound is administered weekly. In some embodiments, about 50 mg of the psychoactive compound is administered every other week. In some embodiments, about 50 mg of the psychoactive compound is administered every third week. In some embodiments, about 50 mg of the psychoactive compound is administered monthly.

In some embodiments, about 100 mg of the psychoactive compound is administered daily. In some embodiments, about 100 mg of the psychoactive compound is administered twice a day. In some embodiments, about 100 mg of the psychoactive compound is administered three times a day. In some embodiments, about 100 mg of the psychoactive compound is administered every other day. In some embodiments, about 100 mg of the psychoactive compound is administered every third day. In some embodiments, about 100 mg of the psychoactive compound is administered every fourth day. In some embodiments, about 100 mg of the psychoactive compound is administered every fifth day. In some embodiments, about 100 mg of the psychoactive compound is administered weekly. In some embodiments, about 100 mg of the psychoactive compound is administered every other week. In some embodiments, about 100 mg of the psychoactive compound is administered every third week. In some embodiments, about 100 mg of the psychoactive compound is administered monthly.

In some embodiments, about 150 mg of the psychoactive compound is administered daily. In some embodiments, about 150 mg of the psychoactive compound is administered twice a day. In some embodiments, about 150 mg of the psychoactive compound is administered three times a day. In some embodiments, about 150 mg of the psychoactive compound is administered every other day. In some embodiments, about 150 mg of the psychoactive compound is administered every third day. In some embodiments, about 150 mg of the psychoactive compound is administered every fourth day. In some embodiments, about 150 mg of the psychoactive compound is administered every fifth day. In some embodiments, about 150 mg of the psychoactive compound is administered weekly. In some embodiments, about 150 mg of the psychoactive compound is administered every other week. In some embodiments, about 150 mg of the psychoactive compound is administered every third week. In some embodiments, about 150 mg of the psychoactive compound is administered monthly.

In some embodiments, about 200 mg of the psychoactive compound is administered daily. In some embodiments, about 200 mg of the psychoactive compound is administered twice a day. In some embodiments, about 200 mg of the psychoactive compound is administered three times a day. In some embodiments, about 200 mg of the psychoactive compound is administered every other day. In some embodiments, about 200 mg of the psychoactive compound is administered every third day. In some embodiments, about 200 mg of the psychoactive compound is administered every fourth day. In some embodiments, about 200 mg of the psychoactive compound is administered every fifth day. In some embodiments, about 200 mg of the psychoactive compound is administered weekly. In some embodiments, about 200 mg of the psychoactive compound is administered every other week. In some embodiments, about 200 mg of the psychoactive compound is administered every third week. In some embodiments, about 200 mg of the psychoactive compound is administered monthly.

In some embodiments, about 250 mg of the psychoactive compound is administered daily. In some embodiments, about 250 mg of the psychoactive compound is administered twice a day. In some embodiments, about 250 mg of the psychoactive compound is administered three times a day. In some embodiments, about 250 mg of the psychoactive compound is administered every other day. In some embodiments, about 250 mg of the psychoactive compound is administered every third day. In some embodiments, about 250 mg of the psychoactive compound is administered every fourth day. In some embodiments, about 250 mg of the psychoactive compound is administered every fifth day. In some embodiments, about 250 mg of the psychoactive compound is administered daily. In some embodiments, about 250 mg of the psychoactive compound is administered weekly. In some embodiments, about 250 mg of the psychoactive compound is administered every other week. In some embodiments, about 250 mg of the psychoactive compound is administered every third week. In some embodiments, about 250 mg of the psychoactive compound is administered monthly.

In some embodiments, an initial dose of a psychoactive compound provided herein is administered, which is then boosted 30 minutes-4 hours later by administering a second dose of the psychoactive compound. In some embodiments, the boosted dose is administered about 30 min after the initial dose. In some embodiments, the boosted dose is administered about 60 min after the initial dose. In some embodiments, the boosted dose is administered about 90 min after the initial dose. In some embodiments, the boosted dose is administered about 120 min after the initial dose. In some embodiments, the boosted dose is administered about 150 min after the initial dose. In some embodiments, the boosted dose is administered about 180 min after the initial dose. In some embodiments, the boosted dose is administered about 210 min after the initial dose. In some embodiments, the boosted dose is administered about 240 min after the initial dose.

In some embodiments, the boosted dose is 10% to 100% in amount of the initial dose. In some embodiments, the boosted dose is the same amount as the initial dose. In some embodiments, the boosted dose is about half of the amount of the initial dose. In some embodiments, this dosing schedule is performed daily. In some embodiments, this dosing schedule is performed twice a day. In some embodiments, this dosing schedule is performed three times a day. In some embodiments, this dosing schedule is performed every other day. In some embodiments, this dosing schedule is performed every third day. In some embodiments, this dosing schedule is performed every fourth day. In some embodiments this dosing schedule is performed every fifth day. In some embodiments, this dosing schedule is performed weekly. In some embodiments, this dosing schedule is performed every other week. In some embodiments, this dosing schedule is performed every third week. In some embodiments, this dosing schedule is performed monthly.

In some embodiments, a dose of a psychoactive compound provided herein may be in the range of about 1 mg/kg to about 100 mg/kg. For example, the dose may be about 1 mg/kg, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 55 mg/kg, about 60 mg/kg, about 65 mg/kg, about 70 mg/kg, about 75 mg/kg, about 80 mg/kg, about 85 mg/kg, about 90 mg/kg, about 95 mg/kg, or about 100 mg/kg. In some embodiments, the dose of a psychoactive compound provided herein is between about 0.1 mg/kg to about 100 mg/kg, 1 mg/kg to about 50 mg/kg, or about 5 mg/kg to about 30 mg/kg. In some embodiments, the dose of a psychoactive compound provided herein is about 1 mg/kg, about 10 mg/kg, or about 25 mg/kg. In some embodiments, the dose of a psychoactive compound provided herein is in the range of about 0.001 mg/kg to about 1 g/kg. In some embodiments, the dose of a psychoactive compound provided herein is in the rage of about 100 mg/kg to about 250 mg/kg. In some embodiments, the dose of a psychoactive compound provided herein is about 25 mg/kg.

In some embodiments, In some embodiments, the psychoactive compound provided herein is administered, e.g., as a single dose or one or more times per week (up to twice daily or even three time a days). In some embodiments, the psychoactive compound provided herein is administered according to a dosing schedule provided herein. In some embodiments, the psychoactive compound provided herein is administered as an extended release or sustained release formulation, for example, to achieve a dosing regimen disclosed herein and releasing 50 mg to 1 g on a set schedule to patients according to the indication(s) being treated in those patients.

The term "subject" refers in one embodiment to a mammal including a human in need of therapy for, or susceptible to, a condition or its sequelae. The subject may include dogs, cats, pigs, cows, sheep, goats, horses, rats, and mice and humans. The term "subject" does not exclude an individual that is normal in all respects.

In some embodiments, the subject is a male. In some embodiments, the subject is a female. In some embodiments, the female subject is pregnant or post-partum. The subject may be a geriatric subject, a pediatric subject, a teenage subject, a young adult subject, or a middle-aged subject. In some embodiments, the subject is less than about 18 years of age. In some embodiments, the subject is at least about 18 years of age. In some embodiments, the subject is about 5-10, about 10-15, about 15-20, about 20-25, about 25-30, about 30-35, about 35-40, about 40-45, about 45-50, about 50-55, about 55-60, about 60-65, about 65-70, about 70-75, about 75-80, about 85-90, about 90-95, or about 95-100 years of age.

As used herein, the singular forms "a," "an," and "the" include plural references unless the context clearly dictates otherwise. For example, the term "a molecule" can also include a plurality of molecules.

Reference to a particular numerical value includes at least that particular value, unless the context clearly dictates otherwise. When a range of values is expressed, another embodiment includes from the one particular value and/or to the other particular value. Further, reference to values stated in ranges include each and every value within that range. All ranges are inclusive and combinable.

The phrase "and/or," as used herein, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements can optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the embodiments, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of."

As used herein, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements can optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

Unless the context indicates otherwise, it is specifically intended that the various features described herein can be used in any combination.

Any patent, patent application publication, or scientific publication, cited herein, is incorporated by reference herein in its entirety.

The following examples are presented in order to more fully illustrate the preferred embodiments of the invention. They should in no way be construed, however, as limiting the broad scope of the invention.

EXAMPLES

Example 1: Effects of Methylone, 2C-B, and MBDB on Fear Extinction Plasticity and Dendritic Architecture in Mice A key question in experimental research is how the short half-life of the compound translates to long-term behavioral changes. One plausible mechanism is neural plasticity. In effect, administration of psychoactive compounds may drive lasting modifications in neural architecture in the brain by strengthening or increasing the number of synaptic connections. Current evidence supporting this view, however, comes mostly from studies of cultured neurons. Still unknown is the extent to which neural plasticity is induced by psychoactive compounds in the mammalian brain, and whether synaptic remodeling occurs in brain regions implicated in neuropsychiatric disorders In this study, the effects of multiple psychoactive medicines are compared in a rodent in vivo model. Multiple conditions are tested, including 3 psychoactive compounds of interest (methylone, 2C-B, and MBDB), in both chronically exposed vs treatment naïve groups (e.g., imipramine, or other antidepressant/anxiolytic agents), a positive control (e.g., another antidepressant/anxiolytic agent), and a vehicle control (saline). The dose-response curves for the psychoactive compounds are characterized by measuring head-twitch response in mice. The plasticity-enhancing effects of administering a single dose of each compound on fear extinction behavior is also determined. Then, the longitudinal effects of administering a single dose of each compound on the density and turnover of dendritic spines is determined using 2-photon imaging microscopy (Shao L X et al. Neuron. 2021 Jun. 25:S0896-6273(21)00423-2. doi: 10.1016/j.neuron.2021.06.008.).

Determine Dose-Response Curves in C57BL/6J Mice

It is important to determine the dose range that is behaviorally relevant for mice. To construct a dose-response curve, head-twitch responses are quantified for a range of doses for the 3 psychoactive compounds (methylone, 2C-B, MBDB) in adult, 6-8 week old C57BL/6J mice, with 40 mice tested per condition. Briefly, animals are placed in arenas inside a sound-attenuated cubicle. The arenas are illuminated with near-infrared lighting. Movements of the mice within all arenas are captured simultaneously by a ceiling-mounted, high-speed camera. Each animal receives an intraperitoneal injection of 1 of 5 doses of one of the compounds—with a dose range selected based on the literature. Mice are assigned randomly to groups. Videos are recorded for ~10 minutes after administration. In a subset of studies, videos are recorded for up to 2 hours to chart the time course. For analyses, head twitches are counted by an experimenter who is blind to the experimental condition. These experiments are used to inform the dose to be used for further studies.

Determine Effects of Methylone, MBDB, and 2C-B on Fear Extinction Plasticity

Neural plasticity may promote alterations in emotional learning. Fear extinction is a behavior in which repeated exposure to an associated fear learning stimulus can reduce the intensity of the fear response, and which may be related to the mechanism of action of these compounds in reducing anxiety or fear. It is not known to what extent novel phenethylamines may enhance fear extinction. Here, the rate of fear extinction is determined after administration of drug in 4 conditions (saline, methylone, 2C-B, MBDB) in adult mice, with 10 mice tested per condition. Briefly, each mouse receives tone-shock pairing (day 1) then on a subsequent day they receive a single administration of the compound (at dose informed by prior study) 30 minutes prior to re-exposure to the fear associated stimulus (day 2). On day 3, fear extinction learning is tested by re-exposing mice again to the associated tone in a fear conditioning apparatus. Fear extinction serves as a model for ameliorating anxiety- and fear-related behaviors in psychiatric disorders and may serve to identify separable behavioral effects from hallucinogenic effects. The circuit mechanisms of potential plasticity enhancement is subsequently addressed in two-photon imaging experiments.

Determine Long-Term Effects on Dendritic Remodeling

Although it has been shown that psychoactive compounds can promote neural plasticity, these experiments study how different compounds induce different degrees of structural remodeling. Here, dendritic spine turnover in medial frontal cortex is determined for 5 conditions (saline, ketamine, methylone, 2C-B, MBDB) in adult mice, with 5 mice tested per condition. Briefly, Thy 1-GFP-M transgenic mice are used, because a sparse subset of cortical pyramidal neurons expresses enhanced green fluorescent protein, allowing for visualization of their dendritic architecture. Each mouse receives a single administration of the compound (at the dose determined above; 10 mg/kg for ketamine). Using a two-photon microscope, dendritic spines in the distal apical tuft branches are imaged and are tracked for 7 sessions at −3, −1, 1, 3, 5, 7, and ~30 days from the day of administration. Imaging the same sets of spines longitudinally allows the determination of the number density of dendritic spines, and also the turnover dynamics including the rates of spine formation and elimination, as well as the fraction of newly formed spines that remain persistent indicating the maturation of a new functional synapse. These results provide data on multiple psychoactive compounds to demonstrate their suitability to treat neuropsychiatric illness.

Example 2: Zebrafish Models of Neuropsychiatric Illnesses

Because of their physiological (neuroanatomical, neuroendocrine, neurochemical) and genetic homology to mammals, robust phenotypes, and value in high-throughput genetic and chemical genetic screens, zebrafish are ideal for developing valid experimental models of major depression, anxiety, and pain disorders to discover novel therapeutics. Behavioral testing approaches, such as approach-avoidance, cognitive, and social paradigms, are available in zebrafish and are useful for identifying depression-like indices in zebrafish in response to physiological, genetic, environmental, and/or psychopharmacological alterations. In addition, the high sensitivity of zebrafish to commonly prescribed psychoactive drugs support the use of this model as a tool for pharmacological research and drug screening. Possessing a fully characterized genome, both adult and larval zebrafish are currently widely used for in vivo screening of various psychoactive medicines.

Zebrafish Reserpine-Induced Depression Model

As a specific inhibitor of monoamine transporters, reserpine is known to deplete monoamine neurotransmitters—confirmed with liquid chromatograph-mass spectrometer analysis—and cause decreased swimming distance and average velocity (hypoactivity), and reduced response to both visual and sound stimuli. Reserpine induces depression-like behavior both in adult zebrafish and in larvae; this is used as an assay for drugs affecting these despair-like states, such as methylone, 2C-B and MBDB. A camera algorithm, Histogram of Oriented Gradient (HOG), analyzes the depression and hypoactivity behavior of zebrafish shoaling to achieve accuracy that is not possible for the human observer.

Zebrafish Anxiety Disorder Models

Many behaviors including anxiety, fear, and stimuli dependent learning can be assessed as early as free-swimming larval stages, whereas social behavior like shoaling and directed aggression, develop with age. Several anxiety tests are done, sequentially or in combination, including an elevated plus maze, novel tank, light-dark box, and open-field test. Known anxiolytic drugs such as benzodiazepines are used as positive controls to assess a drug's effect on levels of diving and exploration behavior, thigmotaxis, hyperactive swimming, erratic swimming, freezing, or avoidance of bright area in adults (scototaxis) and dark area in larval fish.

Example 3: Rodent Models of Neuropsychiatric Illnesses

This Example presents rodent models for several neurological and psychiatric conditions that are used to demonstrate the efficacy of psychoactive compounds described herein. Primate and rodent models have been traditionally used to study cellular mechanisms and neural circuits of hallucinogenic drugs' action.

Depression: Forced Swim Test (FST)

The Forced Swim Test (FST) is a classic, and the most used preclinical behavioral assay to screen compounds with antidepressant-like activity and has high predictive and face validity (Porsolt et al. (1977) *Nature* 266:730-732; Borsini and Meli (1988)*Psychopharmacology* 94:147-160). The premise of the FST is that when rats are placed into a cylinder filled with water, they will initially try to escape, but over time will become immobile. This increased immobility reflects behavioral despair, modeling a depressive-like state. A broad range of antidepressant treatments has been shown to consistently reduce immobility time, with the observation that increases in swimming or climbing correlate with serotonergic or noradrenergic activity, respectively (Detke et al. (1995) *Psychopharmacology* 121:66-72).

Anxiety: Open Field Test (Time Spent in the Center Vs. Periphery)

This behavioral assay, also widely used as an anxiety paradigm, capitalizes on a rodent's innate fear of brightly lit open spaces, which are assumed to induce fear or anxiety. Rodents spend more time hugging the walls of the open field during the test, and these effects correlate to underlying brain regions and mechanisms.

Method: Consecutive beam breaks and/or video-tracking of time spent in the center versus the periphery of the open field are measured. Also measured are parameters such as distance traveled and ambulatory activity (horizontal and vertical) for the duration of the test session.

Results: Anxiolytics such as diazepam increase time spent (and/or distance traveled) in the center of the open field independent of changes in locomotion, used as positive control to assess an agent's effect on these parameters.

Anxiety: Elevated Plus Maze

This behavioral assay, widely used as an anxiety paradigm, is based on unconditioned responses of rodents to a potentially dangerous environment: maze height, luminosity, and open space are assumed to induce fear or anxiety, and to correlate to underlying brain regions and mechanisms.

Method: Video-tracking of time spent in the open arms of the maze to the closed arms, for 5 min starting at the junction. Other ethological parameters include rears, dips, stretched-attend postures.

Results: Anxiolytics such as diazepam increase time spent in open arm activity (duration and/or entries) without decreasing locomotion is used as positive control to assess an agent's effect on these parameters.

Modified Geller Seifter Conflict Test

Rats are trained to lever-press for food under a multiple variable interval-fixed ratio (food; food+shock) schedule of reinforcement. This task generally exhibits good predictive validity for anxiolytic-like compounds, such as diazepam, which increase punished responding (i.e., antagonize response suppression in the punished period). It also exhibits selectivity for anxiolytics, with apparently no effects in other classes and can assess MBDB's anxiolytic effect with a positive control such as Bupropion.

Fibromyalgia: Reserpine-Induced Myalgia Model

Reserpine (1 mg/kg/s.c.) is administered for 3 days to mimic chronic widespread pain and complex symptoms.

Method: Duloxetine (30 mg/kg, p.o.) is administered 60 min before a forced swimming test (FST), then rats are exposed to LDI: a single dose of γ-radiation (0.5 Gy) 1 day before the FST.

Results: Reserpine significantly increases immobility time in the FST, and decreases the amount of 5-hydroxytryptamine, dopamine, and norepinephrine in the cerebral cortex. It also increases malondialdehyde and nitric oxide and reduces glutathione contents in brain tissue. LDI alone or combined with duloxetine completely antagonize reserpine-induced fibromyalgia, as assessed by the measured parameters.

Fibromyalgia: Acid-Saline Model

Allodynia, hyperalgesia, and other associated fibromyalgia-like symptomologies is rapidly induced via acid injection (pH 4.0). Once induced, animals display a hypersensitivity to mechanical and visceral stimulation. Symptoms last a minimum of 14 days post-induction, allowing for evaluation over time, and comparisons with vehicle and positive control (e.g., buprenorphine).

Example 4: Methylone Case Series

This Example is based on a case series of 32 narratives for methylone administered orally in single or multiple dosing sessions by a clinical psychologist in an outpatient therapy setting. The case series is composed of two datasets (Cohort 1 and Cohort 2):

Cohort 1: 4 case narratives in a healthy population providing information on safety and tolerability of methylone administered in a single dosing session.

Cohort 2: 28 case narratives providing efficacy and safety information from consecutive patients with a diagnosis of interest (PTSD or MDD) with baseline assessments. Cohort 2 was evaluated for efficacy post-dosing using the Clinical Global Impression-severity (CGI-S) at baseline and Clinical Global Impression-improvement (CGI-I), as described in more detail below, compared to baseline CGI-S established prior to first methylone dosing. CGI-S scale was also evaluated in a subset of patients from Cohort 2 post-treatment. Cohort 2 was evaluated for any observed or reported safety events following a single dosing session.

Clinical Global Improvement Scale

Clinical Global Impressions (CGI) scale includes 2 components: CGI-S ("severity") and CGI-I ("improvement").

CGI-S Guidelines

1=Normal—not at all ill, symptoms of disorder not present past seven days

2=Borderline mentally ill—subtle or suspected pathology

3=Mildly ill—clearly established symptoms with minimal, if any, distress or difficulty in social and occupational function 4=Moderately ill—overt symptoms causing noticeable, but modest, functional impairment or distress; symptom level may warrant medication 5=Markedly ill—intrusive symptoms that distinctly impair social/occupational function or cause intrusive levels of distress 6=Severely ill—disruptive pathology, behavior and function are frequently influenced by symptoms, may require assistance from others 7=Among the most extremely ill patients—pathology drastically interferes in many life functions; may be hospitalized CGI-I Guidelines
  1=Very much improved—nearly all better; good level of functioning; minimal symptoms; represents a very substantial change
  2=Much improved—notably better with significant reduction of symptoms; increase in the level of functioning but some symptoms remain
  3=Minimally improved—slightly better with little or no clinically meaningful reduction of symptoms. Represents very little change in basic clinical status, level of care, or functional capacity
  4=No change symptoms remain essentially unchanged
  5=Minimally worse—slightly worse but may not be clinically meaningful; may represent very little change in basic clinical status or functional capacity
  6=Much worse—clinically significant increase in symptoms and diminished functioning
  7=Very much worse—severe exacerbation of symptoms and loss of functioning Results Baseline Demographics: Demographics for Cohorts 1 and 2 are presented in Table 1.

TABLE 1

Baseline Demographics

|  | Cohort 1 N = 4 | Cohort 2 N = 28 | PTSD N = 20 | MDD N = 8 | Total N = 32 |
|---|---|---|---|---|---|
| Sex |  |  |  |  |  |
| Male (n, %) | 3 (75) | 12 (43) | 8 (40) | 4 (50) | 15 (47) |
| Female (n, %) | 1 (25) | 16 (57) | 12 (60) | 4 (50) | 17 (53) |
| Race |  |  |  |  |  |
| Caucasian | 4 (100) | 26 (93) | 18 (95) | 8 (100) | 30 (94) |
| Asian | 0 | 2 (7) | 2 (5) | 0 | 2 (6) |
| Age |  |  |  |  |  |
| Mean | 42.5 | 45.9 | 46.9 | 43.3 | 45.4 |
| Median | 41 | 47 | 43 | 48 | 45 |
| IQR | 56 | 21.5 | 20.5 | 29 | 23.3 |
| Min, Max | 28, 60 | 22,78 | 25,78 | 22,76 | 22,78 |
| Range | 32 | 56 | 53 | 54 | 56 |
| Age population |  |  |  |  |  |
| 18-<65 years | 4 (100) | 24 (86) | 17 (85) | 7 (88) | 28 (88) |
| ≥65 years | 0 | 4 (14) | 3 (15) | 1 (13) | 4 (13) |

Abbreviations:
CGI-S = Clinical Global Impression-Severity;
IQR = Interquartile range;
Max = Maximum;
MDD = Major Depressive Disorder;
Min = Minimum;
PTSD = Post Traumatic Stress Disorder Cohort 1 is composed of 4 healthy adult subjects (3 males and 1 female) ranging in age from 28 to 60 years of age who were administered methylone in a single administration in either a group setting (3 subjects) or individually (1 subject). Cohort 1 tended to have a higher proportion of male subjects who were younger, and all were Caucasian. Prior experience with methylone was unknown in two subjects and confirmed in the other two subjects (one male and one female).

Cohort 2 is composed of 28 patients with PTSD or MDD treated in an outpatient setting. Note that one of the patients included in the MDD population had a primary diagnosis of bipolar disorder type I. Overall, males and females were well represented within Cohort 2 and showed similar proportions within the PTSD and MDD subsets.

The age population exceeded 85% for ages 18 to <65 years of age overall and in the subsets for PTSD and MDD with a small subset of elderly patients (≥65 years of age) in the overall data set and the PTSD and MDD subsets. The overall age range for Cohort 2 was wide ranging from 22 to 78 years (mean 45.9 years) with similar distribution among the PTSD and MDD subsets.

Cohort 2 Baseline Disease Characteristics

Primary Diagnosis

Overall, the majority [20 of the 28 patients, (71%)] of the patients included in Cohort 2 had a primary diagnosis of PTSD and 29% had a primary diagnosis of MDD or bipolar disorder (7 MDD; 1 bipolar). However, 10 of the 20 patients (50%) with PTSD also had a secondary diagnosis of MDD or depression (6 MDD; 4 depression) with 64.2% overall having a primary or secondary diagnosis of MDD or depression.

Prior/Concomitant Therapies

For the PTSD subset of Cohort 2, the most common prior/concomitant therapies reported for 2 patients or more in descending order were SSRIs (14 patients), talk therapy (7 patients), breath work (4 patients), cognitive and behavioral therapy and antidepressant unspecified (4 patients each). The majority of patients had discontinued their respective therapies prior to the initial methylone dosing session. Within the PTSD subset, 5 patients had concomitant therapy with SSRIs or other antidepressant classes and 4 of these patients had magnitude of improvement CGI 1 or 2. The treatment regimens were as follows:

fluoxetine 20-40 mg
  fluoxetine (dose unspecified)
  fluoxetine and bupropion (doses unspecified)
  escitalopram (dose unspecified)
  bupropion (dose unspecified)
    Lamotrigine (dose unspecified) discontinued after first of 6 sessions.
    The patient had a quasi-psychedelic experience, but not specified at which session this occurred, as described below in more detail.

For the MDD subset of Cohort 2, the most common prior/current therapies reported for 2 patients or more in descending order were SSRIs (3 patients), talk therapy (3 patients each) psychotherapy (2 patients) and antiepileptics (2 patients). The majority of patients had discontinued their respective therapies prior to the initial methylone dosing session. Only a single patient had concomitant therapies at the time of methylone dosing with unspecified doses of escitalopram, clonazepam, lamotrigine and propranolol which were tapered after the fifth of 10 methylone sessions. Magnitude of improvement was CGI-I 2 and no safety events were reported.

Baseline Disease Severity

Baseline disease severity (CGI-S) for Cohort 2 is shown in Table 2 and FIG. 2. Baseline CGI-S ranged from 4 to 7 and 85.7% of patients had baseline CGI-S 5 or 6 with similar proportion in both the PTSD and MDD subsets.

TABLE 2

Cohort 2 Baseline Disease Severity by CGI-S

|  | PTSD N = 20 | MDD N = 8 | Total N = 28 |
|---|---|---|---|
| CGI-S |  |  |  |
| 4 | 2 | 1 | 3 |
| 5 | 11 | 2 | 13 |

TABLE 2-continued

Cohort 2 Baseline Disease Severity by CGI-S

| | PTSD<br>N = 20 | MDD<br>N = 8 | Total<br>N = 28 |
|---|---|---|---|
| 6 | 5* | 5 | 10* |
| 7 | 2* | 0 | 2* |

Abbreviations:
CGI-S = Clinical Global Impression-Severity;
MDD = Major Depressive Disorder;
PTSD = Post Traumatic Stress Disorder
*One patient included in category "6" had baseline CGI-S "6+" and one patient in category 7 has baseline CGI-S "6 or 7"

Baseline Symptom Inventory

FIG. 1 shows the baseline symptom inventory for symptoms occurring in 2 or more of the 28 patients included in Cohort 2. The most common symptoms included insomnia (12 patients), anhedonia (10 patients), anger (9 patients) and nightmare/night terrors (7 patients).

Methylone Dose and Regimen

Cohort 1

The 3 males in Cohort 1 were dosed in a group setting during a single session with a total methylone dose of 790 mg administered as a regimen of methylone 280 mg followed by booster doses of 190 mg, 190 mg and 130 mg. For the one female healthy volunteer, the total dose was 870 mg administered as methylone 250 mg followed by booster doses of 220 mg, 200 mg, and 200 mg.

Cohort 2

Only sessions that included methylone dosing were counted as dosing sessions. Some patients were noted to continue group therapy with methylone beyond the sessions noted but the magnitude of improvement by CGI-I as compared to baseline was assessed following the methylone dosing sessions.

In two cases, one as an initial session, and one as a second session, MDMA was administered as a single agent. In one case with repeat methylone dosing sessions, the initial session, included co-administration of 3 grams of mushrooms 30 minutes after methylone dosing.

Single sessions occurred for 8 of the 28 cases with no booster in two of these cases. In the remainder of the cases, multiple sessions occurred, and booster doses were used in all or some of the remaining patients (26 cases reports) with multiple booster doses used in some or all of the sessions in 15 patients. Methylone total dose at each session had a minimum range of 100 mg to 690 mg and a maximum range of 180 mg to 1020 mg. Maximum total dose for each session exceeded 500 mg [methylone dose plus booster dose(s)] in only four sessions in 3 patients. The methylone dose ranged from 100 to 270 mg and the booster dose(s) had a total cumulative dose that ranged from 50 mg to 880 mg but only exceeded 370 mg in two sessions in two patients. Individual methylone booster doses had a minimum range of 50 mg to 240 mg and a maximum range of 80 mg to 250 mg.

Safety

Cohort 1

For all 4 subjects in Cohort 1, no adverse effects or after-effects were observed or reported. All 3 males were noted to be able to walk, make tea and had no signs of inebriation.

Cohort 2

In the majority of cases included in Cohort 2 (25 of 28 cases; 89.3%), methylone dosing was well tolerated and no safety events were reported. One case report included an adverse event of increased anxiety following 117 mg MDMA administered in the first session that did not include methylone and occurred prior to any methylone dosing at subsequent sessions and did not recur with methylone dosing at 130 mg total dose (80 mg+50 mg booster). In 3 patients (all ≥65 years of age), adverse events were reported following methylone dosing as follows:

I. Case Report A:
75-year-old male with primary diagnosis of PTSD and medical history of atrial fibrillation and a pacemaker developed lightheadedness during the fifth session using methylone 150 mg and 150 mg booster (highest dose administered) when coming down from the medicine. The event was not considered severe and did not require intervention. Previous total doses ranged from 100-250 mg. There was a negative rechallenge (i.e., repeat methylone dosing) with administration of an unknown dose at home.

II. Case Report B:
70-year-old male with primary diagnosis of PTSD and secondary diagnosis of depression administered methylone 690 mg during a single session (200 mg followed by booster doses 250 mg and 240 mg) did not experience any adverse events during the session but reported adverse events of sleeplessness and loss of appetite following the session, thought to be due to the simulant effects of methylone.

III. Case Report C:
78-year-old male with primary diagnosis of PTSD and secondary diagnosis of anxiety with medical history of "well-regulated cardiovascular issues" administered methylone with a total dose at each session ranging from 100 to 300 mg (100-150 mg methylone with 0 to 150 mg booster) over 5 sessions reported a quasi-psychedelic experience, but dose and further details were not provided. No intervention required.

Efficacy

As Cohort 1 consisted of healthy volunteers, efficacy is reported for Cohort 2 which consisted of PTSD and MDD patients.

Magnitude of Improvement

CGI-I and Time to Initial Improvement

Figure 3A:
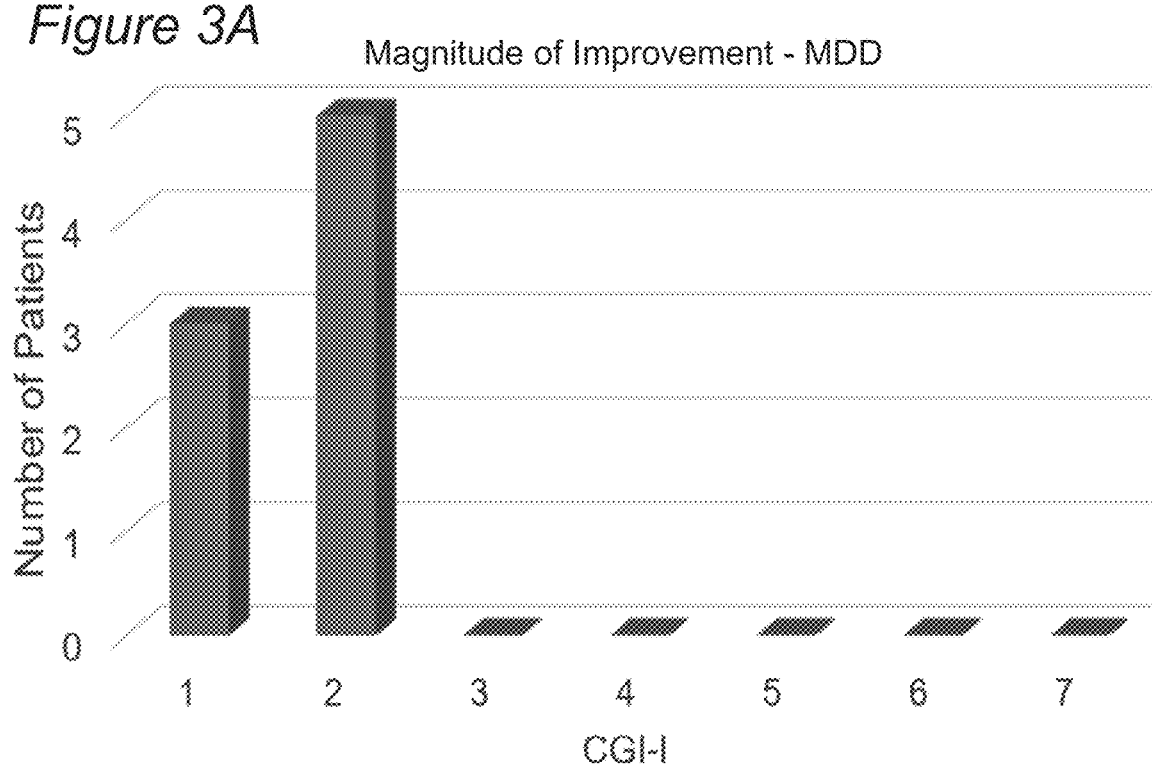
FIGS. 3A-3B show the Magnitude of Improvement in Cohort 2 for subjects in the (FIG. 3A) MDD subset and (FIG. 3B) PTSD subset.
Figure 3B:
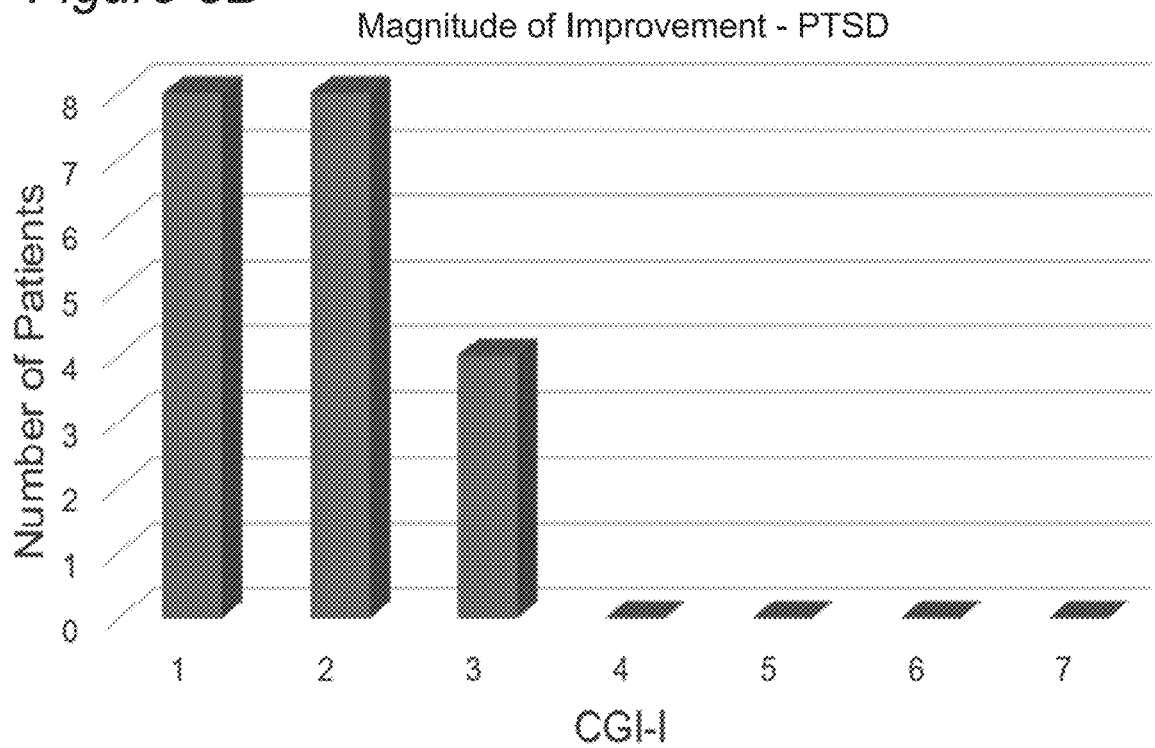

All patients achieved at least minimal improvement (CGI-3 or better) following treatment with methylone. The highest observed magnitude of improvement for the 28 cases included in Cohort 2 is shown in Table 3 and FIG. 3. CGI-I 1 or 2 was achieved in 86% of the patients [16/20 patients (80%) for the PTSD subset and 8/8 patients (100%) for the MDD subset] corresponding to "much improved" or "very much improved" compared to baseline CGI-S. Additionally, initial improvement was observed with the first methylone session in almost 90% of patients (25 of 28 patients). Two additional cases experienced initial improvement following the $2^{nd}$ and $3^{rd}$ sessions, respectively, and one case required 10+ sessions for initial improvement.

TABLE 3

Magnitude of Improvement

| CGI-I | Number of cases<br>(N = 28) |
|---|---|
| 1 | 11* |
| 2 | 13 |
| 3 | 4 |
| 4 | 0 |

TABLE 3-continued

Magnitude of Improvement

| CGI-I | Number of cases (N = 28) |
|---|---|
| 5 | 0 |
| 6 | 0 |
| 7 | 0 |

Abbreviations:
CGI-I = Clinical Global Impression-Improvement
*One case rated as CGI-I "½" and included in the category "1"

Durability of Response

Within the PTSD subset of Cohort 2, 16 of the case narratives included information on durability. One case reported no durable effect, and 15 case narratives reported a durable effect (6 months or greater in 12 of the cases, limited to 3 months in one case and unknown in 2 cases). In one of the cases with unknown length of durable response, the narrative stated that "the subject no longer qualified for the disease' following the $4^{th}$ methylone dosing session.

Within the MDD subset of Cohort 2, 6 of the 8 case narratives included information on durability. One case reported no durable effect, and the remaining 5 cases reported a durable effect which was noted to be 2 years in 2 patients, 5 years in 1 patient and unknown in 2 patients but reported as "stable after 13 sessions" in 1 patient and "sustained" in another patient.

Change in CGI-S

CGI-S post-treatment was only reported in 5 cases as shown in Table 4 including one patient noted to achieve a stable CGI-S 1. One case was noted to sometimes achieve CGI-S 1. In 5 additional case narratives that did not include post-treatment CGI-S scores, it was reported that patients no longer qualified for the diagnosis post-treatment and 5 of these cases achieved CGI-I 1.

TABLE 4

Maximum Change Post-treatment CGI-S

| Case ID # | Pre-treatment Baseline CGI-S | Best CGI-S | CGI-S max change from BL |
|---|---|---|---|
| 2 | 6 | 2 | −4 |
| 3 | 5 | 2* | −3 |
| 6 | 6 | 3 | −3 |
| 7 | 5 | 1 | −3 |
| 21 | 7 | 4 | −3 |

CONCLUSION

Overall methylone, administered in single or multiple sessions with single dosing and/or with booster dose(s) was well tolerated. No safety events were reported in healthy volunteers or adult patients age 18 or <65 years of age. Transient safety events were reported in 3 elderly patients which occurred at high dose or did not recur on rechallenge. One of these events included a quasi-psychedelic experience which occurs in ~5-6 of every 2,000 methylone administrations.

The majority of patients in the PTSD subset (90%) and MDD subset (88%) had baseline CGI-S of 5 or greater ("markedly" or "severely" ill) with 2 of the PTSD patients in the severest category of CGI-S 7 (i.e., amongst the "most severely ill patients"). Despite this, Cohort 2 had a magnitude of improvement of 1 or 2 in 86% of patients overall [16/20 patients (80%) for the PTSD subset and 8/8 patients (100%) for the MDD subset] corresponding to "much improved" or "very much improved" compared to baseline CGI-S.

Example 5: Clinical Evidence for the Use of Methylone in the Treatment of PTSD: A Case Series with Long-Term Follow-Up PTSD is a debilitating, and often chronic, psychiatric disorder characterized by a constellation of symptoms including intrusive memories, distressing dreams, dissociative reactions, physiological reactivity to and avoidance of trauma-related stimuli, negative cognition and mood, lassitude, increased arousal, impaired sleep, cognitive dysfunction, irritability, risk-taking behavior, and clinically significant distress and impairment in functioning. It is estimated that 70% of the world population have been exposed to trauma and, though resilience is the norm rather than the exception, approximately 6% of trauma-exposed individuals develop PTSD. The estimated prevalence of PTSD is 20% following interpersonal violence, 25% in combat-exposed military veterans, 50% in rape survivors, and as high as 86% among certain refugee groups. PTSD is a well-established risk factor for suicide, increasing suicide risk 6 to 29-fold above the general population.

Available pharmacotherapy options are limited. Selective serotonin reuptake inhibitors (SSRIs) represent the first-line pharmacological treatment; paroxetine and sertraline are the only FDA-approved medications for treating PTSD. However, despite their established efficacy, these treatments are sub-optimal. They are slow-acting antidepressants (SAADs) with a delayed onset of action—most patients do not show significant effects until at least 4 weeks (and often up to 8 weeks) of continuous treatment. This latency period is decidedly troubling, as it significantly increases the risk for suicide and self-harm as well as for other potentially destructive behaviors. Even when optimally delivered, 40% of the patients do not respond to SSRIs, and only about 20% to 30% achieve remission, and the magnitude of the difference from placebo ranges from 10% to 20%. The rates of non-response or partial response to these medications among individuals with chronic and complex PTSD such as military veterans, are comparable or worse to those of the civilian patient population. Furthermore, many who are classified as 'treatment-responders' remain symptomatic and continue to lead restricted lives.

Trauma-focused psychotherapy also shows some efficacy in treatment of PTSD and is often the first-line intervention selected, given the known limitations in pharmacotherapy. Prolonged Exposure (PE) and Cognitive Processing Therapy (CPT) are the gold standard treatments, but access to appropriately trained therapists is limited and effective therapy requires a willingness on the part of the patients to expose themselves to trauma-related memories and to experience the attendant distress. The attrition rate among gold-standard psychotherapy outcome studies ranges from 17% to 55.8%, and nonresponse can be as high as 50%. Regardless of treatment modality, troubling symptoms often persist even in patients classified as treatment responders. The efficacy gap may also be particularly significant among Veterans treated in Veterans Affairs (VA) Medical Center settings, perhaps due, at least in part, to the complexity of these patients, whom often have significant psychiatric and medical comorbidities and repeated chronic trauma exposures. There is thus an urgent need to identify rapidly acting novel strategies to treat PTSD, delineate the mechanisms underlying treatment effects, and, critically, establish baseline markers that can predict therapeutic response.

Recently, several placebo-controlled clinical trials have demonstrated an acute and enduring beneficial clinical effect in PTSD, as measured by the Clinician-Administered PTSD Scale for DSM-5 (CAPS-5), after administration of two to three doses of methylenedioxymethamphetamine (MDMA) with manualized psychotherapy. These robust enduring clinical effects were recently replicated in a large Phase 3 clinical trial. A second Phase 3 clinical trial is currently underway, and a favorable clinical outcome could place MDMA-assisted psychotherapy on track for FDA approval.

3,4-methylenedioxy-N-methylcathinone (methylone; also known as MDMC, βk-MDMA, and M1) is a rapid acting empathogen (RAE) structurally related to MDMA. A recent observational-naturalistic study compared the acute pharmacological and physiological effects of orally administered methylone and MDMA in healthy participants with a history of prior exposure to both compounds. While the compounds maybe mechanistically similar, methylone produced less intense prototypical psychostimulant and empathogenic effects, including lessened euphoria, inebriation, stimulant-like effects, and changes in cognitive and body perception, with increased sociability relative to MDMA. The notable differences in acute pharmacological effects could be explained in part by their differences in serotonin (5-HT) receptor affinity. Methylone has significantly lower affinity for $5-HT_{2A}$ than MDMA and has partial agonist activity at the $5-HT_{1A}$ receptor, which MDMA does not. Methylone also has weaker antagonistic effects on $5-HT_{2C}$ relative to MDMA, which has partial agonistic activity. Methylone also inhibits or reverses the monoamine reuptake transporters for dopamine, norepinephrine, and serotonin, which increases extracellular concentrations of these neurotransmitters.

This Example presents a more detailed analysis of 21 patients from the previous Example (the 20 patients from the PTSD subset discussed in the previous Example plus one patient from that Example who was mischaracterized and was subsequently determined to have a primary diagnosis of PTSD) with a primary diagnosis of PTSD, with a range of psychiatric comorbidities, who were treated clinically with methylone in an outpatient setting. The patients were not given structured psychotherapy in conjunction with methylone treatment, which differs from recent studies of MDMA that emphasize the importance of a manualized psychedelic-assisted psychotherapy model. These characteristics, together with methylone's short duration of action and less dramatic acute psychological and physiological effects, make it an attractive agent for clinical use in the treatment of PTSD.

Materials and Methods

Archival clinical data was obtained from 21 patients with a primary diagnosis of PTSD who received one or more oral methylone administrations as part of specialty care in an outpatient psychiatric setting. No protected health information was disclosed and no consent was obtained from patients for the use of their archival data. Case narratives were systematically compiled from data collected as part of routine clinical work. Diagnoses were confirmed by an experienced clinician using semi-structured interviews. Baseline symptom severity was evaluated using the Clinical Global Impressions Scale-Severity (CGI-S). Symptom improvement was evaluated using the Clinical Global Impressions Scale-Improvement (CGI-I) following dosing. Patients were evaluated for any observed or reported safety events following their methylone dosing session(s). Because these case narratives were examined retrospectively from routine clinical care records, and not gathered prospectively in a research study, more specific validated rating scales for assessing PTSD symptoms were not available. Additionally, follow-up varied, with the length of follow-up ranging from one week (Case 2) to 15 years (Case 16).

TABLE 5

Demographic Data, Clinical Characteristics, and Response to Treatment

| ID | Age (years)/ Sex (M/F) | Comorbidities | Prior Treatments | Concomitant Medications | Total Methylone Dose Range Across all Sessions (mg) | # Observed Dosing Sessions | Duration Treatment | Baseline CGI-S | Peak CGI-I (Time since baseline CGI-S) |
|---|---|---|---|---|---|---|---|---|---|
| 2 | 62/M | Bipolar II; GAD; SCZ; Insomnia; SI | Psychotherapy; psychiatric therapy; olanzapine; quetiapine; venlafaxine; Opiates | lamotrigine; lurasidone HCl; clonazepam; amphetamine, dextroamphetamine, propranolol | 550 | 1 | 1 session | 7 | 1 (1 week) |
| 3 | 75/M | Parkinson's Disease; Cardiovascular diagnosis; Atrial fibrillation; Pacemaker | CBT, Breath work, hypnosis, unspecified SSRIs | — | 100 to 300 | 5 | >18 months | 5 | 1 (11 months) |
| 4 | 49/M | MDD; GAD; Social phobia; SI; Insomnia | Talk therapy; CBT; experiential therapy (ketamine); fluoxetine | — | 250 to 620 | 4 | 10 months | 7 | 1 (10 months) |
| 5 | 54/M | Eating disorder (UNSP); Insomnia | Talk therapy; CBT; support group; SSRI (escitalopram) | Escitalopram | 150 to 350 | 3 | 11 months | 5 | 3 (11 months) |

TABLE 5-continued

Demographic Data, Clinical Characteristics, and Response to Treatment

| ID | Age (years)/ Sex (M/F) | Comorbidities | Prior Treatments | Concomitant Medications | Total Methylone Dose Range Across all Sessions (mg) | # Observed Dosing Sessions | Duration Treatment | Baseline CGI-S | Peak CGI-I (Time since baseline CGI-S) |
|---|---|---|---|---|---|---|---|---|---|
| 6 | 38/F | MDD; BPD; SI | Residential clinical therapy including group therapy; breath therapy; talk therapy | — | 400 to 500 | 4 | 2 years | 6 | 1 (16 months) |
| 7 | 52/F | GAD | ~5 years talk therapy 2 experiential treatments each lasting 4 weeks (hug and scream + primal therapy) | — | 150 to 410 | 6 | 1-2 months | 5 | 1 (1 month) |
| 8 | 46/F | N/A | Unspecified SSRIs | — | 230 | 1 | 1 session | 4 | 2 (1st session) |
| 9 | 25/F | MDD; GAD; SI | fluoxetine <60 mg | — | 360 | 1 | 1 session | 6 | 1 (1st session) |
| 10 | 70/M | MDD | Unspecified SSRIs | — | 690 | 1 | 1 session | 5 | 2 (1st session |
| 11 | 33/F | MDD; GAD; binge eating disorder; SI | Talk therapy; CBT; holotropic breathwork; somatic experiencing; inpatient treatment; unspecified SSRIs | Fluoxetine | 310 to 460 | 3 | 5 months | 6 | 1 (5 months) |
| 12 | 78/M | UNSP anxiety disorder; Insomnia | Unspecified antidepressants | bupropion* lamotrigine | 100 to 300 | 5 | 2 years | 5 | 2 (2 months) |
| 13 | 40/M | MDD; anxiety disorder; SI; Insomnia | Wellbutrin; unspecified SSRIs, psychotropics and unspecified narcoleptic | Unspecified SSRI | 330 | 1 | 1 session | 5 | 2 (1st session) |
| 14 | 36/F | Insomnia | Unspecified sleep medication | — | 220 | 1 | 1 session | 5 | 1 (1st session) |
| 15 | 38/F | Substance addiction; SI; insomnia | Detox for alcohol and narcotic abuse; couples counseling; unspecified SSRIs | — | 470 | 1 | 1 session | 6 | 2 (1st session) |
| 16 | 28/M | MDD; UNSP Personality disorder | Holotropic breathwork; weekly therapy; unspecified SSRIs | — | 310 to 1020 | unknown | 3 years with a gap of 15 years, then 2 years | 6 | 3 (2-3 days after each session, but relapsed soon after) |
| 17 | 38/F | N/A | Unspecified SSRIs | — | 300 to 330 | 12+ | 1.5-2 years | 4 | 3 (after 10 sessions, >1 year) |

TABLE 5-continued

Demographic Data, Clinical Characteristics, and Response to Treatment

| ID | Age (years)/ Sex (M/F) | Comorbidities | Prior Treatments | Concomitant Medications | Total Methylone Dose Range Across all Sessions (mg) | # Observed Dosing Sessions | Duration Treatment | Baseline CGI-S | Peak CGI-I (Time since baseline CGI-S) |
|---|---|---|---|---|---|---|---|---|---|
| 18 | 25/M | N/A | | Unspecified psychotropic | 150 | 1 | 1 session | 5 | 3 (1st session) |
| 19 | 58/F | MDD; UNSP Anxiety | Several inpatient treatments; weekly therapy sessions; unspecified SSRI combination therapy | — | 250 to 400 | 5 | 10 months | 5 | 2 (8 months) |
| 20 | 59/F | MDD | Talk therapy; meditation, unspecified SSRIs, recreational psychedelics | — | 180 to 400 | 3 | 9 months | 5 | 1 (9 months) |
| 21 | 58/F | MDD; UNSP anxiety; social phobia; SI | Prior inpatient treatment; multiple psychiatric modalities; Multiple Medications | — | 100 | 1 | 1 session | 7 | 2 (1st session) |
| 22 | 38/F | N/A | Inpatient treatment; unspecified SSRI | — | 250 to 360 | 4 | 3.5 years | 5 | 2 (1 year) |

*Case 12: Based on the case narrative, it is unknown if bupropion was a prior or concomitant medication.
Abbreviations: BPD: Borderline personality disorder; CBT: cognitive behavioral therapy; F: female; GAD: generalized anxiety disorder; M: male; MDD: major depressive disorder; NR: not reported; PTSD: posttraumatic stress disorder; SCZ: Schizophrenia; SSRI: selective serotonin reuptake inhibitor; SNRI: serotonin-norepinephrine reuptake inhibitor; SI: suicidal ideation; UNSP: unspecified Results Methylone produced acute and enduring improvements in both PTSD and depression symptoms, without any notable lasting adverse effects. Clinical data are presented in Table 5. Twelve patients (57%) were female; 19 (90%) were White. The mean age was 47.6 years (range: 25 to 78). Baseline CGI-S scores ranged between 4 and 7 for all 21 patients (i.e., moderately to severely ill; see FIG. 4). Six patients (28.6%) were on concomitant SSRI or other psychotropic therapy at the time of methylone dosing. This is notable because recent trials of MDMA in PTSD have required that patients be on no other psychotropic medications, as SSRI antidepressants have been shown to attenuate the therapeutic effects of MDMA due to substrate competition. All patients were experiencing debilitating symptoms despite past and/or ongoing psychological and pharmacological treatment. Prior therapies included: SSRIs/SNRIs (n=14; 66.7%), supportive unstructured therapy (n=8; 38%), structured cognitive and behavioral therapy (n=4; 19%), and unspecified antidepressant therapy (n=3; 14.3%).

Figure 4A:
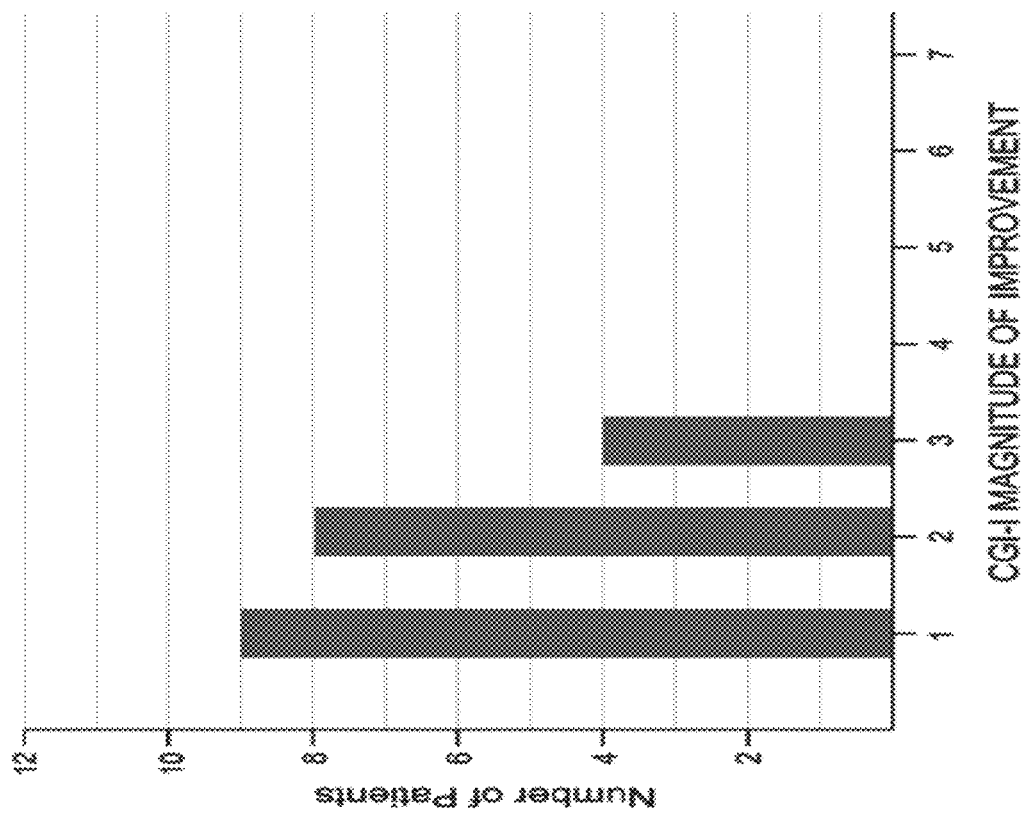
FIGS. 4A-4B show the (FIG. 4A) Baseline Disease Severity and (FIG. 4B) Magnitude of Improvement for the patients of Example 5.
Figure 4B:
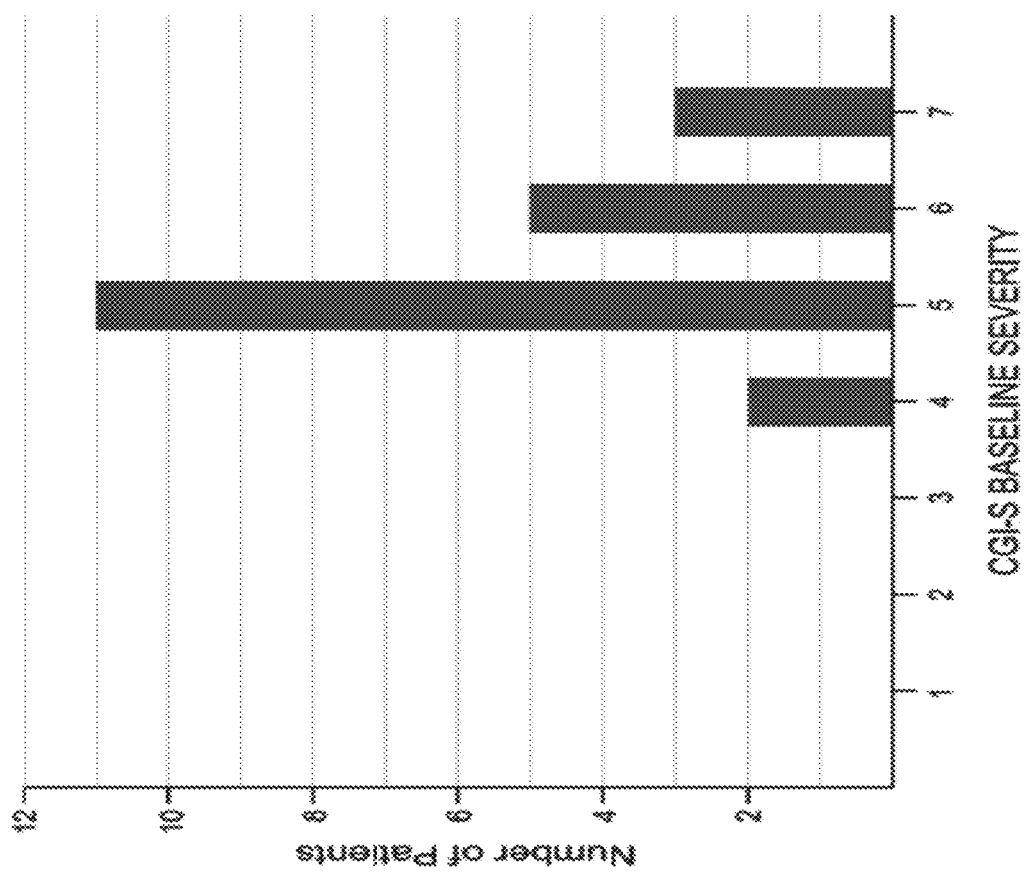

All 21 patients achieved at least minimal improvement (CGI-I 1, 2 or 3) following methylone treatment, with 17 achieving a CGI-I of 1 (very much improved, 9 patients) or 2 (much improved, 8 patients; see FIG. 4). This trend was observed even for patients who received only a single dose of methylone (n=9), where 8 patients (89%) achieved CGI-I scores of 1 or 2. For patients with multiple methylone dosing sessions (n=12), initial improvement was noted after the initial session in 83% (n=10) of the patients; one additional patient experienced improvement after the second session.

Information on durability of the clinical effect was captured for 17 of 21 patients. One individual reported no durable effect (i.e., symptom severity returned to baseline almost immediately), and 16 reported a durable effect (>six months in 11 patients) and one patient each reported a sustained effect of three months, two months, and one week respectively. In one of the four case narratives that did not include durability information, the patient "no longer qualified for the disease (i.e., PTSD)" following the 4th methylone dosing session (10 months after baseline assessment), as determined by the treatment team.

Dosing summary: Methylone was administered orally. Other medications were not changed during methylone treatment. In many cases, an additional, booster dose of methylone was administered 1 hour after the initial dose to extend the therapeutic window and optimize clinical response. In several cases, treatment was continued and, in some cases, the dose was further escalated in later sessions (see Table 5). Booster doses were included for 19 patients in one or more of the sessions. Starting doses were between 100 and 270 mg, and these as well as booster doses were selected based on clinical judgement.

Safety: Methylone was generally well tolerated, and no patients discontinued treatment due to adverse events. A total of four adverse events were noted in three of the 21 patients (two in one patient); none were considered severe, and none required medical intervention. A 75-year-old male with a medical history of stable atrial fibrillation (with a pacemaker) and Parkinson's Disease developed lightheadedness around the end of his fifth session using methylone, at a total dose of 300 mg (150 mg followed by booster dose of 150 mg, which was the highest dose administered for this patient). This symptom resolved quickly, and the individual was feeling well upon discharge with no other adverse effects. A 70-year-old male administered methylone 690 mg during a single dosing session (200 mg followed by booster doses of 250 mg and 240 mg) did not experience any adverse events during the session but reported sleeplessness and loss of appetite the night following the session. These symptoms had resolved by the following day. A 78-year-old male reported a flashback-like experience during one treatment session. This patient participated in 5 dosing sessions with a total methylone dose at each session ranging from 100 to 300 mg.

Patient reports: A 62-year-old male patient with treatment-refractory PTSD (ID=Case 2 in Table 5) who received methylone in conjunction with ongoing treatment with SSRI noted after the first dosing session that "[his] problems are seemingly disappearing, and maybe more in the head than actual . . . [and that] the treatment with methylone is like a new 'window into hope' that makes the idea of suicide foolish and unnecessary." Following a rapid and sustained reduction in PTSD symptoms after a single methylone session, he expressed interest in tapering off his SSRI as it was no longer needed. Another patient, a 52-year-old female patient with treatment-refractory PTSD and comorbid generalized anxiety disorder (ID=Case 7 in Table 5) described one session as "the healing of the inner little girl." She expressed the recognition that "PTSD isn't going to rule [her] life anymore. [She is] there for that inner child, and she communicated with [her], and [they] have healed [their PTSD]."

DISCUSSION

In this case series of patients with a primary diagnosis of PTSD, with a high rate of comorbidity and prior treatment attempts, methylone produced rapid symptom improvement, as measured by CGI-I. The majority (90%) had baseline CGI-S of 5 or greater ("markedly" or "severely" ill), with 3 patients in the category of CGI-S of 7 (i.e., amongst the "most severely ill patients"). The majority (81%) of patients achieved scores per CGI-I corresponding to "much improved" or "very much improved" (FIG. 4). These effects are similar to those seen in recent controlled clinical trials of MDMA in conjunction with manualized psychotherapy for PTSD, in which rapid and robust improvements were observed in severely ill, complex, and treatment-resistant patients.

Methylone was well-tolerated over a broad dose range (100 to 1,020 mg), with one to ten administrations. A few adverse events were reported in three older patients, age 70 and over; these were mild and required no intervention. No patients discontinued methylone treatment because of adverse events. Notably, none of these adverse events occurred in patients receiving concomitant SSRI therapy.

Strengths and Limitations: This is the first report of methylone administration in patients with PTSD. This case series provides evidence that methylone has utility in the pharmacological treatment of PTSD. However, these data have certain limitations. These participants were treated clinically; data for this report were collected retrospectively from review of clinical records. Dosing and follow-up were variable and there was no randomization, control, or blinding to treatment condition. Further, the sample lacks diversity and ongoing psychotherapy and medication adjustment during the variable follow-up period may have influenced clinical course. A strength of this report is the complexity of the sample, which aids in generalizability. Despite these limitations, these case narratives in a complex patient population constitute the first clinical evidence for the efficacy of methylone to treat of PTSD.

Methylone has not received the same cultural or clinical attention as MDMA, perhaps due to its milder and shorter psychopharmacological effects (e.g., euphoria, empathogenic effects). However, these "softer" effects may be particularly helpful for some patients who are not appropriate for treatment with the more intense acute psychological and physiological effects of MDMA.

Example 6: Methylone in the FST: Implications for Depression, Anxiety, and PTSD

In this Example, whether methylone could produce a fast-acting antidepressant-like effect in the rat FST was investigated and the prototypical selective serotonin reuptake inhibitor (SSRI) fluoxetine was used as an antidepressant control.

Methods

Animals: Male Sprague Dawley rats (Charles River Laboratories) weighing 180-200 g on arrival, were used for this study which took place at Melior Discovery (Exton, PA). Rats acclimated to their home cages for at least one week before testing, were maintained in a controlled environment on a 12 h light/dark cycle, with no more than 2 rats per cage. Animals received ad libitum access to food and water and were assigned randomly to treatment groups. Animal use and procedures were in accordance with established protocols approved by the IACUC committee, Melior Standard Operation Procedures (SOP), and Transcend Therapeutics.

Forced Swim Test (EST): In the FST trial, rats were be placed in a circular plexiglass container filled with water, with no means of escape. Water temperature was maintained at 22-25° C. and changed for every animal. After an acclimation period, rats were timed for inactivity (failure to struggle), activity, swim time and climbing time. Day 1 consisted of a 15 min acclimation trial, and Day 2 (24 h later) consisted of the 5 min test. A time sampling procedure was employed where animals were observed every 5 sec and scored for immobility, swimming, or climbing. Fluoxetine (10 mg/kg, IP, Sigma Aldrich) or 0.9% sterile saline vehicle (vehicle 3× group) were administered 23.5, 5, and 1 h before testing in the FST. Methylone (5, 15, or 30 mg/kg, IP; Cayman Chemical) or 0.9% saline vehicle (vehicle 1× group) were administered 30 min prior to FST testing. The experimenter was blinded to treatment.

Binding Studies: Radioligand binding was performed using standard protocols using [$^3$H]citalopram, [$^3$H] WIN35428, and [$^3$H]nisoxetine for serotonin (5HT), dopamine (DA), and norepinephrine (NE) transporters, respectively. Radiolabeled 5HT, NE, and DA uptake and release studies in rat brain synaptosomes were conducted using standard protocols.

Statistical Analysis: Data for each parameter of the test (immobility, swimming, or climbing) is expressed as the mean±SEM. Differences between groups were determined by one-way ANOVA and post-hoc Tukey's test with a p-value of less than 0.05 indicating statistically significant differences.

Results and Conclusions

A single dose of methylone produced a robust, dose-dependent and fast-acting antidepressant-like response in the rat FST (FIG. 5). Notably, 2-3 injections of an SSRI antidepressant are generally required to elicit a behavioral response in the FST, as demonstrated by the fluoxetine control group in the current study that received 3 doses of fluoxetine prior to testing (FIG. 5). However, rats treated with a single dose of methylone 30 minutes before testing in the FST showed highly significant reductions in immobility (FIG. 5A). Notably, a single dose of methylone (5, 15, or 30 mg/kg, IP) administered 30 min prior to testing reduced immobility by 54, 99, or 96%, respectively, compared to rats receiving saline vehicle (p<0.0001). Mid and high doses of methylone significantly increased swimming (FIG. 5B). Climbing was only increased at the lowest dose of methylone, reflecting recruitment of noradrenergic receptor activity at this dose level (FIG. 5C).

The magnitude of the effect of mid and high doses of methylone (99% and 96% reductions) was notably greater than fluoxetine (56%, FIG. 5A). These data also demonstrate that methylone out-performs other psychedelic drugs. Previous reports of ketamine administration show 30% (Hibicke et al. (2020) *ACS Chem. Neurosci* 11: 864-871), 25-55% (Yang et al. (2013) *Ups J Med Sci* 118: 3-8), or 60% (Tizabi et al. (2012) *Neuroscience* 213: 72-80) reductions in immobility (reviewed by Weston et al. (2021) *Frontiers in Psychiatry* 12: 659052.). LSD and psilocybin have been shown to reduce immobility in the FST by 38% and 67%, respectively (Hibicke et al., 2020). MDMA (5 or 10 mg/kg) has been reported to reduce immobility by 45% and 78% in Sprague Dawley rats, respectively (Majumder et al. (2011) *Behav Pharmacol* 22:758-65.) but had a more robust effect in Flinders Sensitive Line rats, a genetic model for depression (45% and 93%, respectively, id.). Binding studies confirmed methylone binding at the 5HT, NE, and DA transporters.

Figure 6:
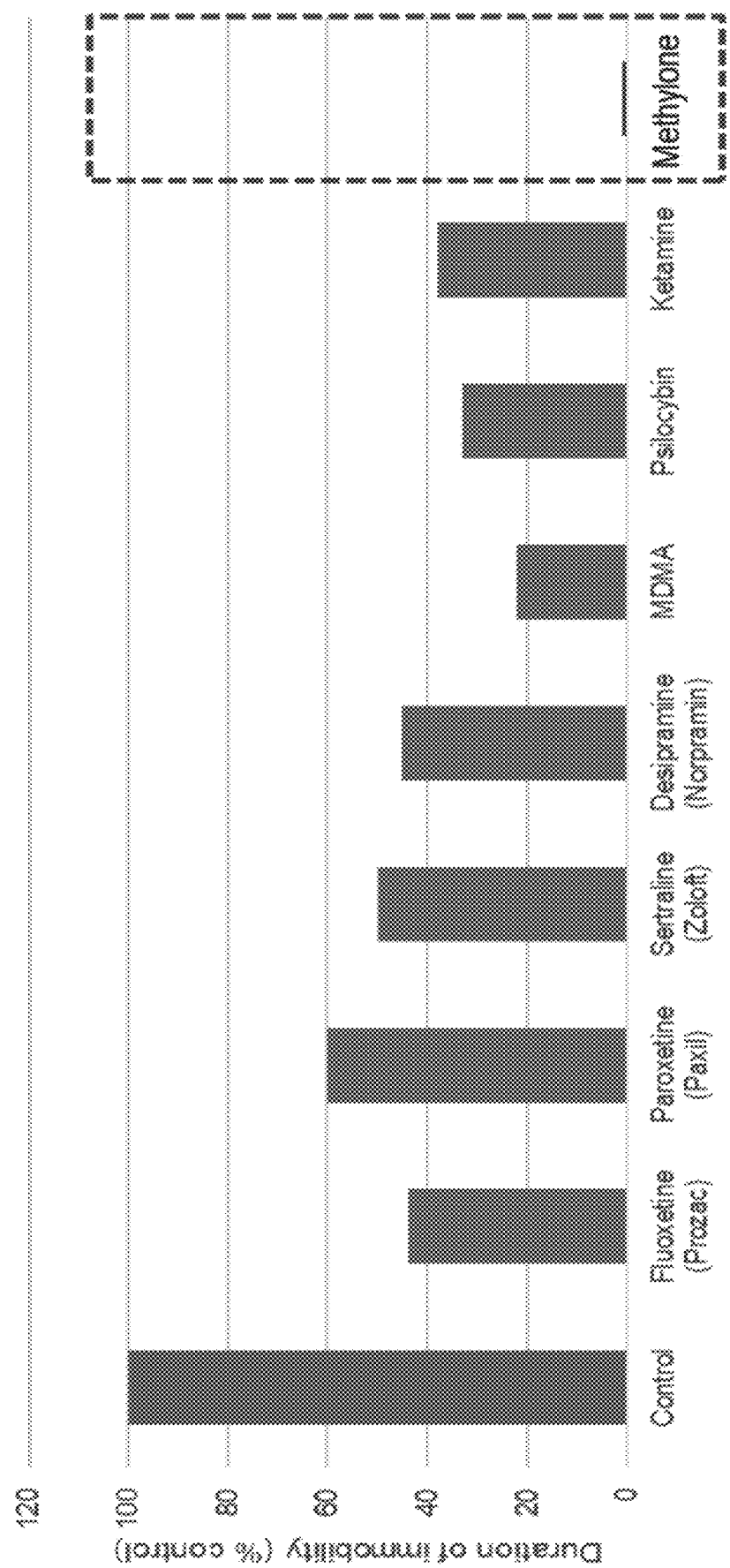
FIG. 6: Methylone outperforms other antidepressants in the Forced Swim Test.

In summary, methylone produced a more robust antidepressant-like response than the SSRI fluoxetine in the FST, a canonical behavioral assay with well-established specificity and selectivity for antidepressant drugs. The magnitude of methylone's effect in this test also surpassed that of other psychedelics and antidepressants tested in wild-type rats in the literature (FIG. 6). Despite its structural similarity to MDMA, methylone shows distinct effects on monoamine transporter binding, uptake and release.

Taken together, these results show the utility of methylone in the treatment of depression and other CNS disorders where antidepressants are efficacious, including but not limited to post-traumatic stress disorder (PTSD), mood disorders, anxiety disorders, obsessive compulsive disorder (OCD), and fibromyalgia.

Example 7: 2C-B in the FST: Implications for Depression, Anxiety, and PTSD

In this Example, whether 2C-B could produce a fast-acting antidepressant-like effect in the rat Forced Swim Test (FST) was investigated and the prototypical selective serotonin reuptake inhibitor (SSRI) fluoxetine was used as an antidepressant control.

Methods

Animals: Male Sprague Dawley rats (Charles River Laboratories) weighing 180-200 g on arrival, were used for this study which took place at Melior Discovery (Exton, PA). Rats acclimated to their home cages for at least one week before testing, were maintained in a controlled environment on a 12 h light/dark cycle, with no more than 2 rats per cage. Animals received ad libitum access to food and water and were assigned randomly to treatment groups. Animal use and procedures were in accordance with established protocols approved by the IACUC committee, Melior Standard Operation Procedures (SOP), and Transcend Therapeutics.

Forced Swim Test: In the FST trial, rats were be placed in a circular plexiglass container filled with water, with no means of escape. Water temperature was maintained at 22-25° C. and changed for every animal. After an acclimation period, rats were timed for inactivity (failure to struggle), activity, swim time and climbing time. Day 1 consisted of a 15 min acclimation trial, and Day 2 (24 h later) consisted of the 5 min test. A time sampling procedure was employed where animals were observed every 5 sec and scored for immobility, swimming, or climbing. Fluoxetine (10 mg/kg, IP, Sigma Aldrich) or 0.9% sterile saline vehicle (vehicle 3× group) were administered 23.5, 5, and 1 h before testing in the FST. 2C-B (2.5, 10, or 20 mg/kg, IP, Cayman Chemical) or 0.9% saline vehicle (vehicle 1× group) were administered 30 min prior to FST testing. The experimenter was blinded to treatment.

Statistical Analysis: Data for each parameter of the test (immobility, swimming, or climbing) is expressed as the mean±SEM. Differences between groups were determined by one-way ANOVA and post-hoc Tukey's test with a p-value of less than 0.05 indicating statistically significant differences.

Results and Conclusions

A single mid- or high-dose injection of 2C-B produced a fast-acting antidepressant-like response in the rat FST, while there was no effect at the lowest dose (FIG. 7). Typically, 2-3 injections of an SSRI antidepressant are required to elicit a behavioral response in the FST, as demonstrated by the fluoxetine control group in the current study that received 3 doses of fluoxetine prior to testing (FIG. 7). It is notable that rats receiving a single dose of 2C-B 30 minutes before testing in the FST showed a statistically significant reduction in immobility (FIG. 7A) and accompanying significant increase in swimming (FIG. 7B), consistent with serotonergic activity. The magnitude of the effect of both mid- and high-doses of 2C-B (50% and 53%, respectively) were almost identical to the fluoxetine control group (56%). Climbing was significantly decreased only in the high-dose group receiving 2C-B (FIG. 7C), but the interpretation of this result is unclear.

In summary, 2C-B produced a faster acting antidepressant-like response that is comparable in magnitude to the SSRI fluoxetine in the FST, a canonical behavioral assay with well-established specificity and selectivity for antidepressant drugs. These results show the utility of 2C-B in the treatment of depression and other CNS disorders where antidepressants are efficacious, including but not limited to post-traumatic stress disorder (PTSD), anxiety disorders, obsessive compulsive disorder (OCD), and fibromyalgia.

Example 8: Prior Selective Serotonin Reuptake Inhibitor (SSRI) Treatment does not Interfere with Efficacy of Methylone in the Rat Forced Swim Test Example 6 shows that Methylone produces a rapid, robust dose-dependent antidepressant-like effect in the Forced Swim Test (FST), greater in magnitude than any other antidepressant tested in this model. Selective serotonin reuptake inhibitors (SSRIs) are a first-line treatment for a variety of Central Nervous System (CNS) disorders including post-traumatic stress disorder (PTSD), Major Depressive Disorder (MDD), anxiety disorders, obsessive compulsive disorder (OCD), and fibromyalgia. MDMA-assisted psychotherapy is in clinical trials for the treatment of PTSD, with the caveat that SSRIs inhibit the efficacy of the MDMA-assisted therapy (Feduccia et al. (2021) *Psychopharmacology* 238:581-588.). If a patient requires MDMA-assisted therapy, they will need to stop taking their SSRI treatment. Since SSRIs require a tapered withdrawal period over many weeks, it could take a significant period of time off medication before a patient could begin MDMA treatment. This poses both logistical and safety risks for the most severely affected individuals with PTSD. Since SSRIs prevent the clinical efficacy of MDMA-assisted psychotherapy, in this Example, whether prior administration of the prototypical SSRI fluoxetine affected the behavioral response to Methylone in the FST was investigated.

Methods

Animals: Male Sprague Dawley rats (Charles River Laboratories) weighing 180-200 g on arrival, were used for this study which took place at Melior Discovery (Exton, PA). Rats acclimated to their home cages for at least one week before testing, were maintained in a controlled environment on a 12 h light/dark cycle, with no more than 2 rats per cage. Animals received ad libitum access to food and water and were assigned randomly to treatment groups. Animal use and procedures were in accordance with established protocols approved by the IACUC committee, Melior Standard Operation Procedures (SOP), and Transcend Therapeutics.

Figure 8B:
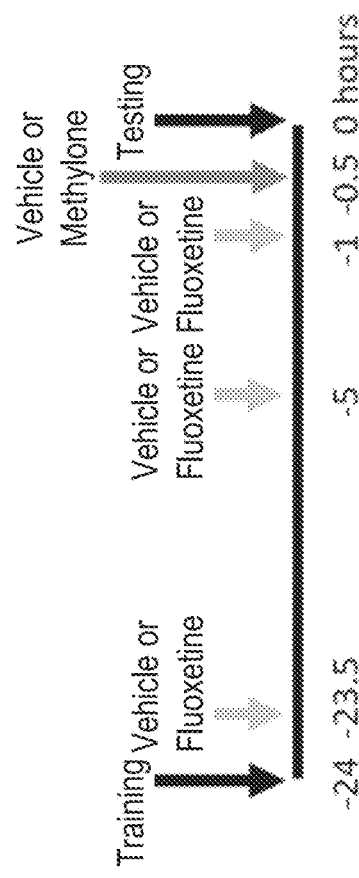
FIGS. 8A-8D: Methylone has a robust antidepressant-like effect in the Forced Swim Test.
Figure 8A:
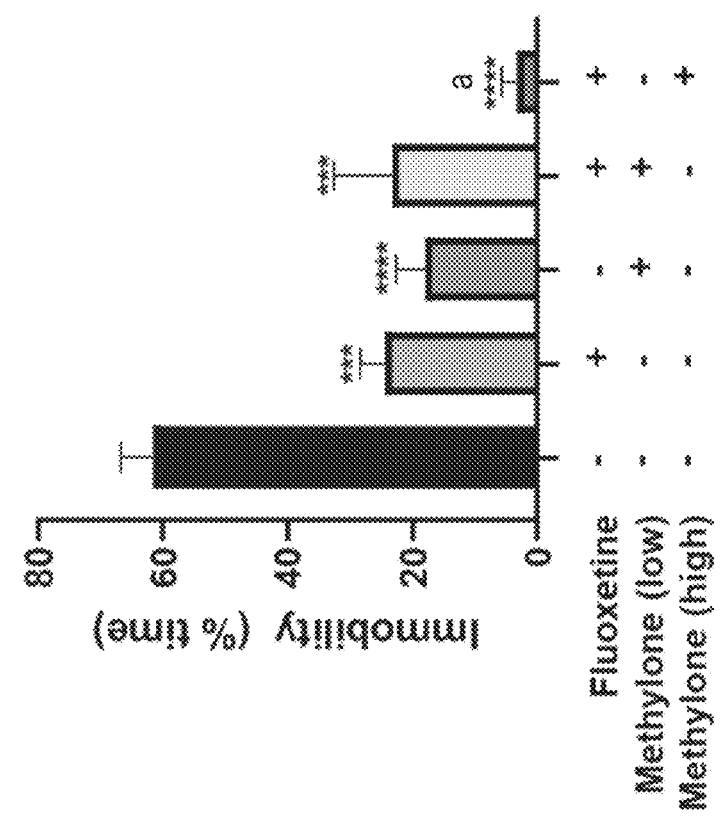

Drug Treatment: Fluoxetine (10 mg/kg, IP, Sigma Aldrich) or 0.9% sterile saline vehicle were administered 23.5, 5, and 1 h before testing in the FST. Methylone (5 or 15 mg/kg, IP; Cayman Chemical) or 0.9% saline vehicle were administered 30 min prior to FST testing (FIG. 8A). Control animals received fluoxetine alone, methylone alone, or saline vehicle. The lower dose of Methylone (5 mg/kg) was focused on because it produced a sub-maximal response in the FST, permitting the potential detection of changes in immobility that could occur in either direction.

Forced Swim Test: In the FST trial, rats were be placed in a circular plexiglass container filled with water, with no means of escape. Water temperature was maintained at 22-25° C. and changed for every animal. After an acclimation period, rats were timed for inactivity (failure to struggle), activity, swim time and climbing time. The experimenter and scorer were blind to treatment group. Day 1 consisted of a 15 min acclimation trial, and Day 2 (24 h later) consisted of the 5 min test. A time sampling procedure was employed where animals were observed every 5 sec and scored for immobility, swimming, or climbing.

Statistical Analysis: Data for each parameter of the test (immobility, swimming, or climbing) is expressed as the mean±SEM. Differences between groups were determined by one-way ANOVA and post-hoc Tukey's test with a p-value of less than 0.05 indicating statistically significant differences.

Results and Conclusions

Three prior doses of fluoxetine had no effect on the immobility in response to a single dose of Methylone (62% reduced immobility vs. vehicle; FIG. 8B; $F_{(4,31)}=17.05$, p<0.0001). Consistent with the results of Example 6, fluoxetine and Methylone (5 mg/kg) both reduced immobility by 60% (p<0.001) and 71% (p<0.0001), respectively, compared to vehicle. Notably, combined treatment with a higher dose of Methylone (15 mg/kg) reduced immobility by 95% compared to vehicle (p<0.0001), which was consistent with Example 6.

Figure 8D:
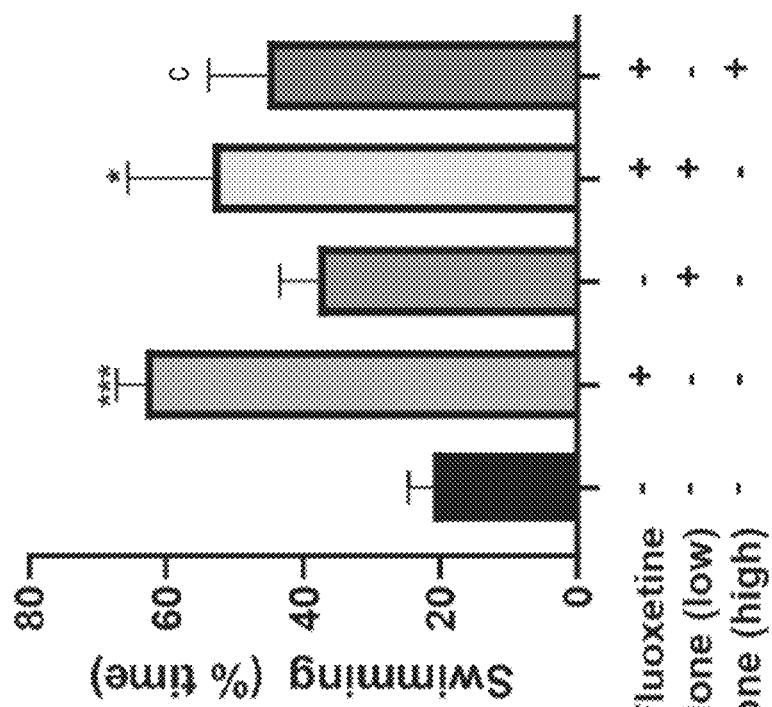
Figure 8C:
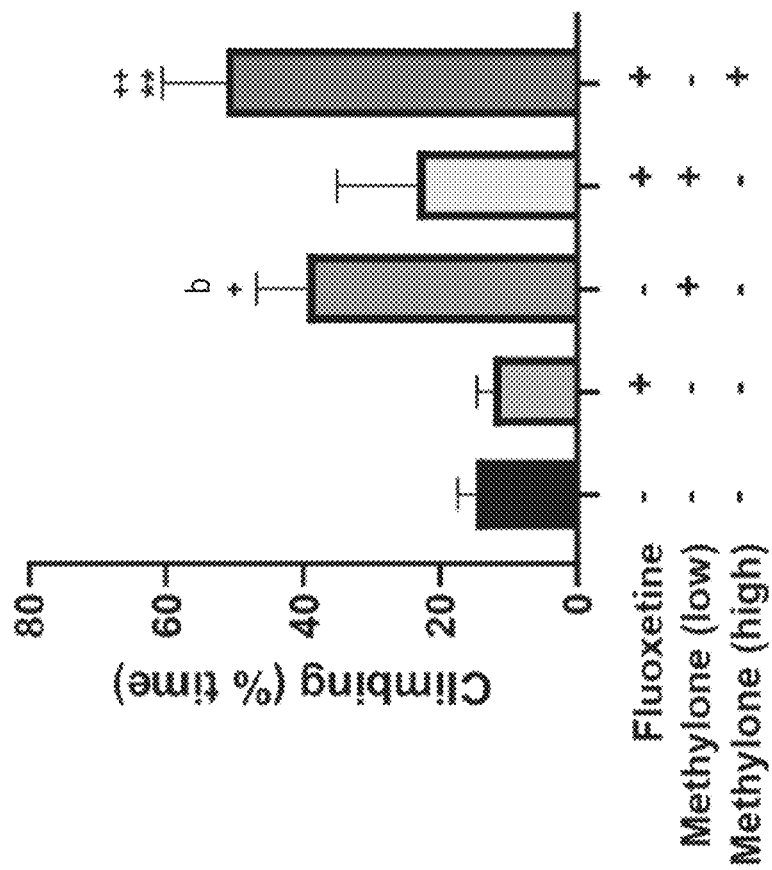

Methylone significantly increased climbing behavior (FIG. 8C; $F_{(4,31)}=5.786$, p<0.01) and fluoxetine significantly increased swimming behavior (FIG. 8D; $F_{(4,31)}=6.063$, p<0.01), consistent with noradrenergic and serotonergic activity, respectively.

In summary, prior treatment with an SSRI (fluoxetine) was investigated and does not affect the behavioral response to Methylone in the rat FST. These findings differentiate Methylone from MDMA and suggest that, unlike with MDMA, an SSRI does not interfere with Methylone's behavioral efficacy. Since SSRIs are the first-line treatment for many CNS disorders, including PTSD, these findings are particularly encouraging, as they suggest that patients could continue taking the SSRIs while taking Methylone potentially without concerns of reduced efficacy.

Example 9: Effects of Methylone, 2-CB and MBDB in a Mouse Model of Post-Traumatic Stress Disorder (PTSD)

Deficient fear extinction memory is a feature of PTSD in patients (Wicking et al. (2016) *Neurobiology of Learning and Memory* 136:116). SSRI antidepressants, similar to the two approved for the treatment of PTSD (i.e., paroxetine and sertraline), prevent fear memory generalization and enhance extinction (Pedraza et al. (2019) *Transl Psychiatry* 9:53). The enhancement of fear extinction might also underlie the beneficial effect of MDMA as a PTSD treatment (Feduccia & Mithoefer (2018) *Progress in Neuro-Psychopharmacology & Biological Psychiatry* 84(Part A), 221-228).

Effective PTSD treatments facilitate the disassociation between a traumatic memory and the patient's fear response, making cues for the traumatic memory evoke less of a fear response. This is modeled in the mouse fear extinction paradigm (see FIG. 9A) which takes place over 3 days. On day 1 (fear conditioning), mice are trained to acquire a "traumatic memory," namely associating the conditioned stimulus (CS, tone) to the unconditioned stimulus (US, foot shock). On day 2 (extinction training), they are trained to forget the traumatic memory association by presenting the CS 6 times (with no US) in a novel environment. On day 3 (extinction recall), the mice are "asked" if that tone (CS) still elicits a fearful response, as measured by the time spent freezing when the tone is presented. Less time freezing means better extinction recall. Drugs that improve extinction recall reduce freezing time on day 3, and, therefore, show potential as a PTSD treatment.

Work with MDMA shows that after fear conditioning, administering MDMA (7.5 mg/kg) 30 minutes prior to extinction training enhances extinction recall measured as 35% reduced freezing compared to saline injected controls (Young et al. (2015) *Transl Psychiatry* 5:e634).

Figure 9A:
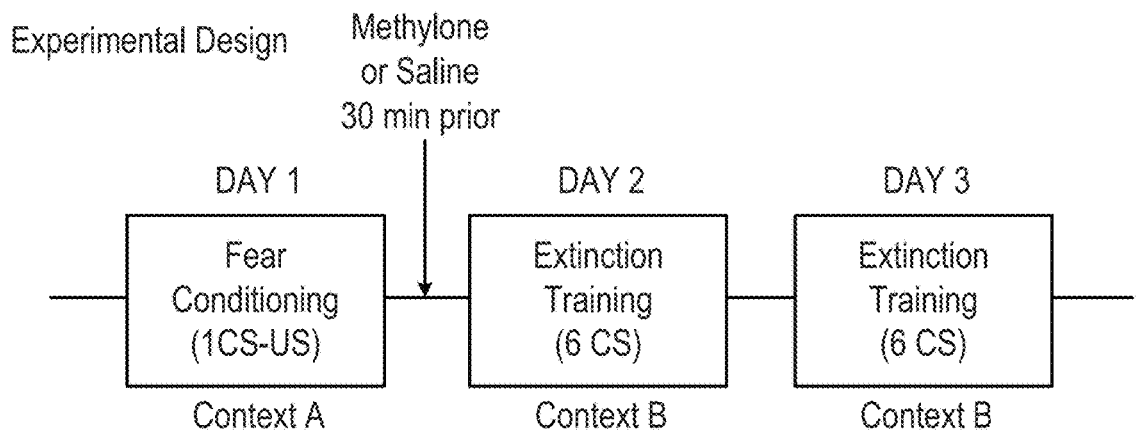
FIGS. 9A-9C: Methylone improves fear extinction recall in a PTSD mouse model.
Figure 9B:
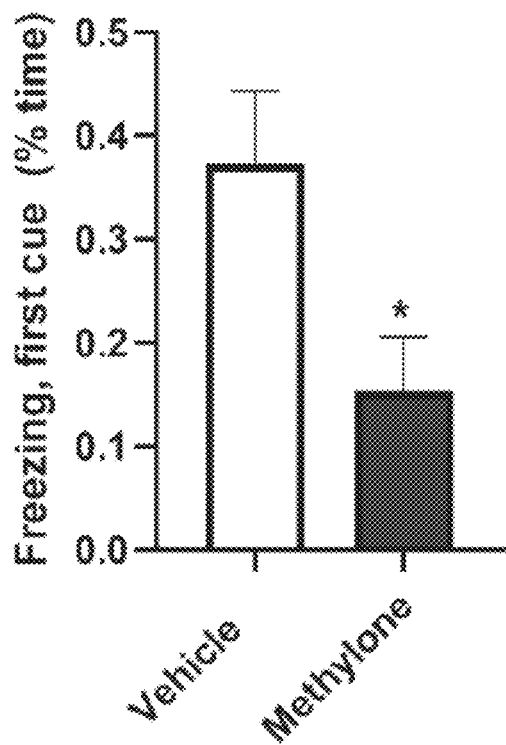
Figure 9C:
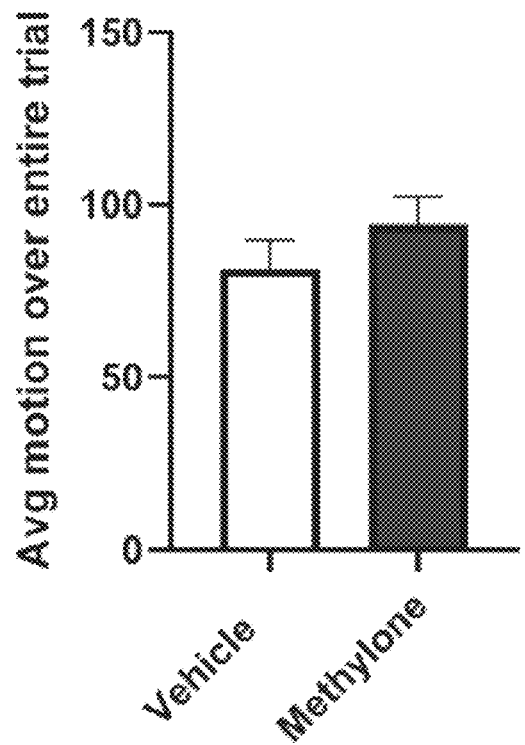

Using an experimental design as depicted in FIG. 9A, the results show that methylone (30 mg/kg) significantly enhances fear extinction recall by nearly 60% compared to saline controls (FIG. 9B). Because effects on locomotor activity could confound the interpretation of these results, it is notable that there were no differences between groups in locomotion recorded for the duration of the testing session (FIG. 9C).

Using an analogous experimental design to the one outlined in FIG. 9A, MBDB was also tested in the fear extinction model of PTSD. Mice given a single injection of MBDB (5 mg/kg, IP) showed improved extinction acquisition on the first trial of extinction training on day 2 (FIG.

Figure 10A:
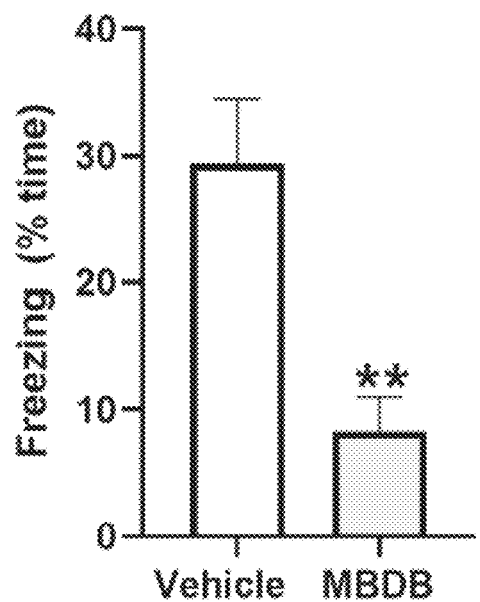
FIGS. 10A-10B: MBDB improves fear extinction in a mouse model of PTSD. A single CS-US (tone-shock) pairing on day 1 was followed by 6 conditioned stimulus (CS) presentations in a novel context (context B). MBDB or saline vehicle was injected 30 min prior to extinction training on day 2. The time spent freezing to the CS was quantified on day 2.
Figure 10B:
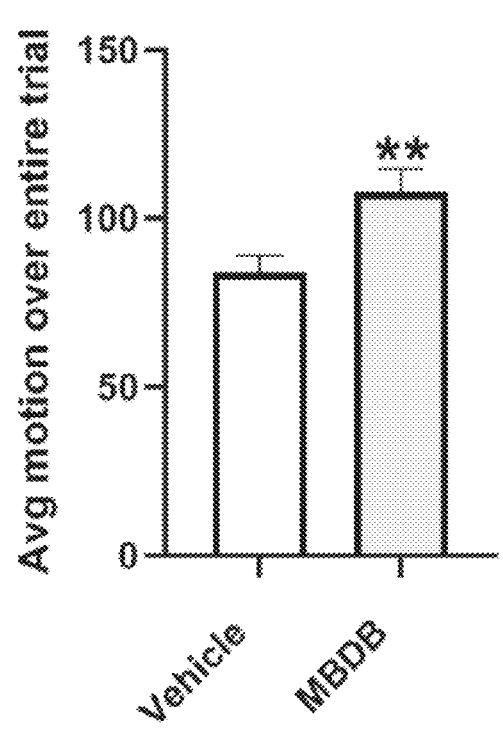

10A) and an accompanying small, but significant increase in locomotor activity on day 2 (FIG. 10B).

Example 10: Prior Selective Serotonin Reuptake Inhibitor (SSRI) Treatment does not Interfere with Efficacy of Methylone in the Rat Forced Swim Test The open field test (OFT) capitalizes on a rodent's innate fear of open spaces to assess anxiety-like behavior. More time spent in the center of an open field reflects an anxiolytic (anti-anxiety) effect.

Figure 11B:
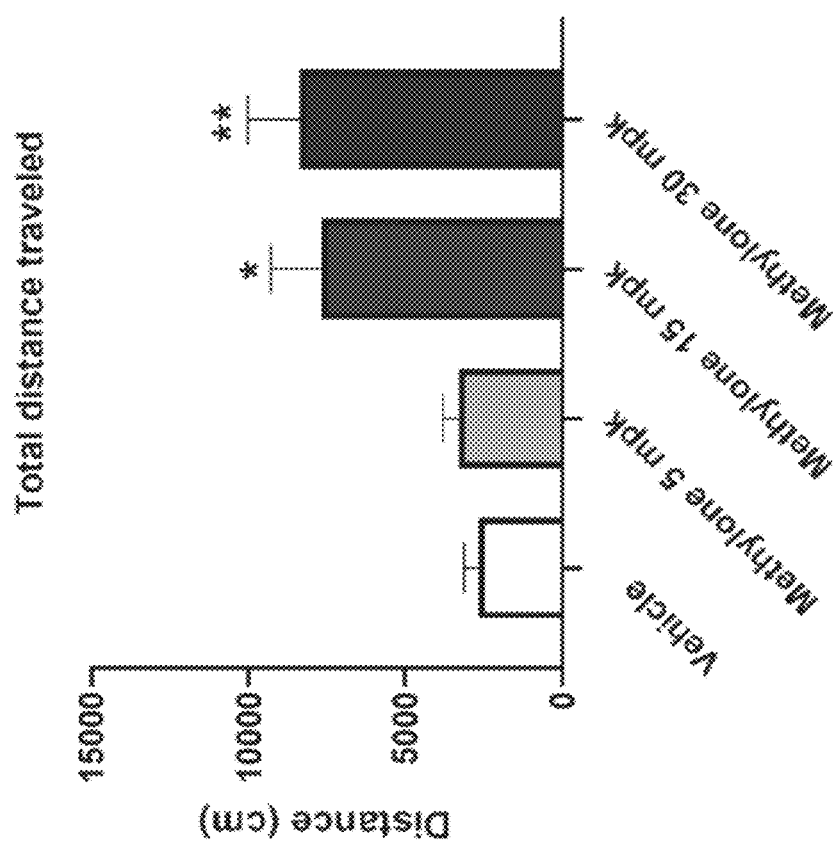
FIGS. 11A-11B: Methylone reduces anxiety and increases locomotion in the open field test. Rats received a single injection of methylone 30 min prior to a 30 min test in the open field.
Figure 11A:
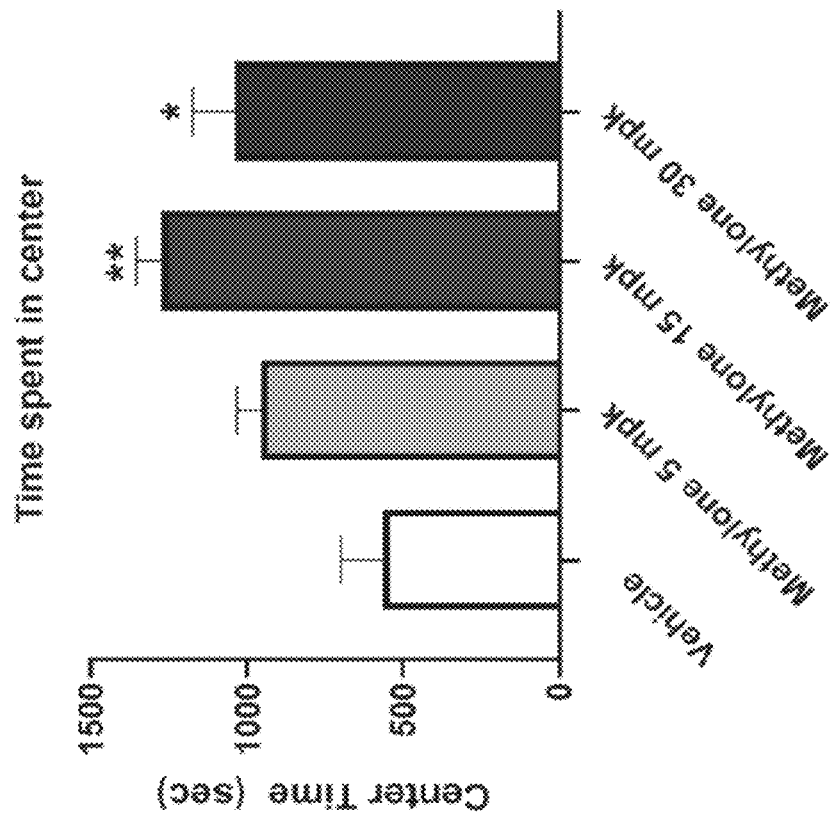

A single methylone dose (5 or 15 mg/kg, IP) administered 30 minutes before testing significantly increases the time spent in the center of the open field compared to vehicle treated controls (FIG. 11A). Locomotor activity was also measured in the OFT. There was no effect of a 5 mg/kg methylone dose compared to vehicle controls, but a significant increase in locomotor activity with 15 or 30 mg/kg methylone doses (FIG. 11B). It will be appreciated by those skilled in the art that changes could be made to the embodiments described above without departing from the broad inventive concept thereof. It is understood, therefore, that this invention is not limited to the particular embodiments disclosed, but it is intended to cover modifications that are within the spirit and scope of the invention, as defined by the appended claims.

What is claimed is:

1. A method of treating a Depressive Disorder and/or ameliorating a symptom thereof in a subject in need thereof, comprising: administering to the subject a therapeutically effective amount of a pharmaceutical composition comprising MBDB (N-methyl-1-(1,3-benzodioxol-5-yl)-2-aminobutane) or a pharmaceutically acceptable salt thereof, and/or an enantiomer thereof, and/or a polymorph thereof.

2. The method of claim 1, wherein MBDB is administered in a dose of 50-1,000 mg.

3. The method of claim 1, wherein MBDB is administered in a dose of 0.8-30 mg/kg.

4. The method of claim 1, wherein the subject is suicidal.

5. The method of claim 1, wherein the Depressive Disorder neuropsychiatric illness is treatment-resistant.

6. The method of claim 1, wherein the MBDB is used in combination with an additional therapy for the Depressive Disorder.

7. The method of claim 6, wherein the additional therapy is psychotherapy.

8. The method of claim 6, wherein the additional therapy comprises administering one or more additional psychoactive agents to the subject.

9. The method of claim 8, wherein the additional psychoactive agents are selected from the group consisting of SSRIs, TCAs, MAOIs, SNRIs, SDNRIs, and anxiolytics.

10. The method of claim 9, wherein the additional psychoactive agent is a selective-serotonin reuptake inhibitor (SSRI).

11. The method of claim 1, wherein the MBDB is administered daily.

12. The method of claim 1, wherein the MBDB is administered weekly.

13. The method of claim 1, wherein the administering step comprises administering an initial dose of MBDB, which is then boosted 30 minutes-4 hours later by administering a second MBDB dose in an amount that is about 10%-100% of the initial dose.

14. The method of claim 1, wherein the Depressive Disorder is selected from the group consisting of Disruptive Mood Dysregulation Disorder, Major Depressive Disorder, Single and Recurrent Episodes, Persistent Depressive Disorder (Dysthymia), Premenstrual Dysphoric Disorder, Substance/Medication-Induced Depressive Disorder, Depressive Disorder Due to Another Medical Condition, Other Specified Depressive Disorder, Unspecified Depressive Disorder, and combinations thereof.

15. A method of treating an Anxiety Disorder and/or ameliorating a symptom thereof in a subject in need thereof, comprising: administering to the subject a therapeutically effective amount of a pharmaceutical composition comprising MBDB (N-methyl-1-(1,3-benzodioxol-5-yl)-2-aminobutane) or a pharmaceutically acceptable salt thereof, and/or an enantiomer thereof, and/or a polymorph thereof.

16. The method of claim 15, wherein the Anxiety Disorder is selected from the group consisting of Generalized anxiety disorder, Panic disorder, Panic attack, Phobic anxiety disorders, Illness Anxiety Disorder, dissociative, stress-related, somatoform other nonpsychotic mental disorders, acute stress reaction, transient adjustment reaction, neurasthenia, psychophysiologic disorders, Obsessive-compulsive disorder, Reaction to severe stress and adjustment disorders, Separation Anxiety Disorder, episodic paroxysmal anxiety, Selective Mutism, Specific Phobia, Social Anxiety Disorder (Social Phobia), Agoraphobia, Substance/Medication-Induced Anxiety Disorder, Anxiety Disorder Due to Another Medical Condition, Anxiety in pregnancy and childbirth, Anxiety in pregnancy antepartum (before childbirth), Anxiety postpartum, Animal type phobia, Arachnophobia, Other animal type phobia, Natural environment type phobia, Fear of thunderstorms, Fear of blood, Fear of injections and transfusions, Fear of other medical care, Fear of injury, Situational type phobia, Claustrophobia, Acrophobia, Other Unspecified Anxiety Disorder, Body Dysmorphic Disorder, Hoarding Disorder, Trichotillomania (Hair-Pulling Disorder), Excoriation (Skin-Picking), and combinations thereof.

17. The method of claim 15, wherein MBDB is administered in a dose of 50-1,000 mg.

18. The method of claim 15, wherein MBDB is administered in a dose of 0.8-30 mg/kg.

19. The method of claim 15, wherein the subject is suicidal.

20. The method of claim 15, wherein the Anxiety Disorder is treatment-resistant.

21. The method of claim 15, wherein the MBDB is used in combination with an additional therapy for the Anxiety Disorder.

22. The method of claim 21, wherein the additional therapy is psychotherapy.

23. The method of claim 21, wherein the additional therapy comprises administering one or more additional psychoactive agents to the subject.

24. The method of claim 23, wherein the additional psychoactive agents are selected from the group consisting of SSRIs, TCAs, MAOIs, SNRIs, SDNRIs, and anxiolytics.

25. The method of claim 24, wherein the additional psychoactive agent is a selective-serotonin reuptake inhibitor (SSRI).

26. The method of claim 25, wherein the subject is taking or is continuing to take the SSRI concurrently with the MBDB.

27. The method of claim 15, wherein the MBDB is administered daily.

28. The method of claim 15, wherein the MBDB is administered weekly.

29. The method of claim 15, wherein the administering step comprises administering an initial dose of MBDB, which is then boosted 30 minutes-4 hours later by administering a second MBDB dose in an amount that is about 10%-100% of the initial dose.

\* \* \* \* \*